United States Patent
Kikuchi

(10) Patent No.: US 10,521,909 B2
(45) Date of Patent: Dec. 31, 2019

(54) INFORMATION PROCESSING SYSTEM, INFORMATION PROCESSING METHOD, AND PROGRAM

(71) Applicant: CANON KABUSHIKI KAISHA, Tokyo (JP)

(72) Inventor: Toru Kikuchi, Hino (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/481,165

(22) Filed: Apr. 6, 2017

(65) Prior Publication Data
US 2017/0301092 A1 Oct. 19, 2017

(30) Foreign Application Priority Data

Apr. 13, 2016 (JP) .................................. 2016-080607

(51) Int. Cl.
| | | |
|---|---|---|
| G06T 7/00 | (2017.01) | |
| G06T 11/60 | (2006.01) | |
| G06T 7/11 | (2017.01) | |
| G06T 7/246 | (2017.01) | |
| G06F 19/00 | (2018.01) | |
| G16H 15/00 | (2018.01) | |

(52) U.S. Cl.
CPC .......... *G06T 7/0016* (2013.01); *G06F 19/321* (2013.01); *G06T 7/11* (2017.01); *G06T 7/248* (2017.01); *G06T 11/60* (2013.01); *G16H 15/00* (2018.01); G06T 2207/10116 (2013.01); G06T 2207/30096 (2013.01)

(58) Field of Classification Search
CPC ......... G06T 7/0016; G06T 7/248; G06T 7/11; G06T 11/60; G06T 2207/30096; G06T 2207/10116; G16H 15/00; G06F 19/321
See application file for complete search history.

(56) References Cited

U.S. PATENT DOCUMENTS

2007/0041623 A1* 2/2007 Roehrig ................ G06F 19/321
382/128
2008/0270183 A1* 10/2008 Hawkins ............... G06F 19/321
705/2

(Continued)

FOREIGN PATENT DOCUMENTS

| JP | 2002-116910 A | 4/2002 |
|---|---|---|
| JP | 2013-157034 A | 8/2013 |
| JP | 2015-179319 A | 10/2015 |

*Primary Examiner* — Tapas Mazumder
(74) *Attorney, Agent, or Firm* — Canon U.S.A., Inc., IP Division

(57) ABSTRACT

An information processing system includes one or more processors; a receiving unit configured to receive a divide instruction for dividing first medical information corresponding to a first display image representing a target region to extract a part of details of the first medical information if the first medical information and the first display image are displayed in association with each other on a display unit; and a display processing unit configured to, if the divide instruction has been received, display the part of details on the display unit newly as second medical information that is different from the first medical information and to display a second display image representing a target region corresponding to the part of details in association with the second medical information on the display unit.

19 Claims, 37 Drawing Sheets

(56) References Cited

U.S. PATENT DOCUMENTS

| | | | |
|---|---|---|---|
| 2013/0308839 A1* | 11/2013 | Taylor | G06F 19/321 |
| | | | 382/128 |
| 2014/0098092 A1* | 4/2014 | Isokawa | G06T 15/08 |
| | | | 345/419 |
| 2014/0267430 A1* | 9/2014 | Kudo | A61B 8/462 |
| | | | 345/649 |
| 2017/0220745 A1* | 8/2017 | Lee | G06F 19/00 |

* cited by examiner

FIG. 3B

| | | | | | |
|---|---|---|---|---|---|
| PATIENT NAME | SIMOMARUKO TARO | AGE | 75 | EXAMINATION TYPE | CONTRAST-ENHANCED CT | EXAMINATION DATE | AUG 23, 2015, 11:23 |
| PATIENT ID | P12345-26789 | SEX | MALE | PART TO BE EXAMINED | THORACOABDOMINAL PART | COMMENT | FOLLOW UP FOR PNEUMONIA |

320 — 321 — 322 — 230b

MAY 19, 2015, 9:46 — 330

REASON FOR EXAM: LUNG CANCER DETAILED EXAMINATION — 332a

| REPRESENTATIVE IMAGE | FINDINGS | DIAGNOSIS | RECOMMENDATION |
|---|---|---|---|
| 333a | PULMONARY MULTIPLE NODULES ARE SEEN. NODULE ON RIGHT LUNG S2I5 ... (334a) | SUSPECTED PNEUMONIA. (335a) | PLEASE FOLLOW UP. (336a) |

AUG 23, 2015, 11:23 — 340

REASON FOR EXAM: FOLLOW UP FOR PNEUMONIA — 332b

| REPRESENTATIVE IMAGE | FINDINGS | DIAGNOSIS | RECOMMENDATION |
|---|---|---|---|
| 333b | PULMONARY MULTIPLE NODULES ARE SEEN. NODULE ON RIGHT LUNG S2I5 ... (334b) | SUSPECTED PNEUMONIA. (335b) | PLEASE FOLLOW UP. (336b) |

350 — 351 — 352 — 353

[TIME-SERIES DISPLAY]  [QUIT WITHOUT SAVING]  [SAVE TEMPORARILY]  [SAVE PERMANENTLY]

FIG. 5

| | RADIOGRAPHIC INTERPRETATION REPORT INFORMATION | | ~500 |
|---|---|---|---|
| MEDICAL INFORMATION 1 | INFORMATION TYPE | REPORT IDENTIFICATION INFORMATION | |
| | REPORT ID | P12345-26789 | |
| | RADIOGRAPHIC INTERPRETATION PHYSICIAN | OHTA HANAKO | |
| | RADIOGRAPHIC INTERPRETATION DATE AND TIME | AUG 23, 2015, 11:30:28 | |
| MEDICAL INFORMATION 2 | INFORMATION TYPE | PATIENT INFORMATION | |
| | PATIENT NAME | SIMOMARUKO TARO | |
| | PATIENT ID | P12345-26789 | |
| | AGE | 75 | |
| | SEX | MALE | |
| MEDICAL INFORMATION 3 | INFORMATION TYPE | EXAMINATION INFORMATION | |
| | EXAMINATION TYPE | CONTRAST-ENHANCED CT | |
| | PART TO BE EXAMINED | THORACOABDOMINAL PART | |
| | EXAMINATION DATE | AUG 23, 2015, 11:23:45 | |
| | COMMENT | FOLLOW UP FOR PNEUMONIA | |
| MEDICAL INFORMATION 4 | INFORMATION TYPE | REASON FOR EXAM | |
| | UID | 1.3.12.2.1107.5.1.4.4853 ... | |
| | DETAILS | FOLLOW UP FOR PNEUMONIA | |
| MEDICAL INFORMATION 5 | INFORMATION TYPE | REPRESENTATIVE IMAGE | |
| | UID | 1.3.12.2.1107.5.1.4.4854 ... | |
| | ROI UID | 1.3.12.2.1107.5.1.4.4854 ... | |
| | ROI UID | 1.3.12.2.1107.5.1.4.4854 ... | |
| ⋮ | ⋮ | ⋮ | |
| MEDICAL INFORMATION i | INFORMATION TYPE | FINDINGS | |
| | UID | 1.3.12.2.1107.5.1.4.1234 ... | |
| | FREE TEXT | 1: PULMONARY MULTIPLE NODULES ARE SEEN. ... | |
| | PART | BOTH LUNGS | |
| | LESION TYPE | MULTIPLE NODULES | |
| ⋮ | ⋮ | ⋮ | |
| MEDICAL INFORMATION j | INFORMATION TYPE | DIAGNOSIS | |
| | UID | 1.3.12.2.1107.5.1.4.233532 ... | |
| | FREE TEXT | SUSPECTED PNEUMONIA. | |
| | NAME OF DIAGNOSED DISEASE | LUNG CANCER | |
| ⋮ | ⋮ | ⋮ | |
| MEDICAL INFORMATION k | INFORMATION TYPE | RECOMMENDATION | |
| | UID | 1.3.12.2.1107.5.1.4.5678 ... | |
| | FREE TEXT | PLEASE FOLLOW UP. | |
| ⋮ | ⋮ | ⋮ | |
| MEDICAL INFORMATION l | INFORMATION TYPE | ROI | |
| | UID | 1.3.12.2.1107.5.1.4.233532 ... | |
| | COORDINATES | X=..., Y=... | |
| | ROI NUMBER | 1 | |
| ⋮ | ⋮ | ⋮ | |
| RELATIONSHIP INFORMATION 1 | RELATIONSHIP TYPE | SUCCESSION | |
| | SOURCE (UID) | 1.3.12.2.1107.5.1.4.0234 ... | |
| | DESTINATION (UID) | 1.3.12.2.1107.5.1.4.1234 ... | |
| RELATIONSHIP INFORMATION 2 | RELATIONSHIP TYPE | CAUSE/BASIS | |
| | SOURCE (UID) | 1.3.12.2.1107.5.1.4.1234 ... | |
| | DESTINATION (UID) | 1.3.12.2.1107.5.1.4.2335.2 ... | |
| ⋮ | ⋮ | ⋮ | |

| | | |
|---|---|---|
| PATIENT NAME | SIMOMARUKO TARO | AGE 75 |
| PATIENT ID | P12345-26789 | SEX MALE |

| EXAMINATION TYPE | CONTRAST-ENHANCED CT | EXAMINATION DATE | AUG 23, 2015, 11:23 |
|---|---|---|---|
| PART TO BE EXAMINED | THORAX | COMMENT | ABNORMAL PART WAS FOUND BY THORAX X-RAY ... |

320

330 — MAY 19, 2015, 9:48

REASON FOR EXAM: LUNG CANCER DETAILED EXAMINATION

REPRESENTATIVE IMAGE — 333a

FINDINGS — 334a
PULMONARY MULTIPLE NODULES ARE SEEN ...
NODULE ON RIGHT LUNG S2 IS ...

DIAGNOSIS — 335a
SUSPECTED PNEUMONIA

RECOMMENDATION — 336a
PLEASE FOLLOW UP.

332a

340 — AUG 23, 2015, 11:23

REASON FOR EXAM: FOLLOW UP FOR PNEUMONIA

REPRESENTATIVE IMAGE — 333b

FINDINGS — 334b
PULMONARY MULTIPLE NODULES ARE SEEN ...
NODULE ON RIGHT LUNG S2 IS ... — 700b

DIAGNOSIS
SUSPECTED PNEUMONIA — 335b
SUSPECTED LUNG CANCER — 335c
NODULE ON RIGHT LUNG S2 IS ... — 601

RECOMMENDATION — 336b
PLEASE FOLLOW UP.

332b

TIME-SERIES DISPLAY   QUIT WITHOUT SAVING   SAVE TEMPORARILY   SAVE PERMANENTLY

FIG. 7B

| PATIENT NAME | SIMOMARUKO TARO | AGE | 75 | | EXAMINATION TYPE | CONTRAST-ENHANCED CT | EXAMINATION DATE | AUG 23, 2015, 11:23 |
| PATIENT ID | P12345-26789 | SEX | MALE | | PART TO BE EXAMINED | THORAX | COMMENT | ABNORMAL PART WAS FOUND BY THORAX X-RAY …. |

MAY 19, 2015, 9:49
REASON FOR EXAM: LUNG CANCER DETAILED EXAMINATION — 332a

REPRESENTATIVE IMAGE | FINDINGS | DIAGNOSIS | RECOMMENDATION
333a | PULMONARY MULTIPLE NODULES ARE SEEN …. NODULE ON RIGHT LUNG S2 IS …. (334a) | SUSPECTED PNEUMONIA (335a) | PLEASE FOLLOW UP (336a)

AUG 23, 2015, 11:23
REASON FOR EXAM: FOLLOW UP FOR PNEUMONIA — 332b

REPRESENTATIVE IMAGE | FINDINGS | DIAGNOSIS | RECOMMENDATION
333c, 333d | PULMONARY MULTIPLE NODULES ARE SEEN …. (334c) / NODULE ON RIGHT LUNG S2 IS …. (334d) | SUSPECTED PNEUMONIA (335b) / SUSPECTED LUNG CANCER (335c) | PLEASE FOLLOW UP (336b)

335b

[TIME-SERIES DISPLAY] [QUIT WITHOUT SAVING] [SAVE TEMPORARILY] [SAVE PERMANENTLY]

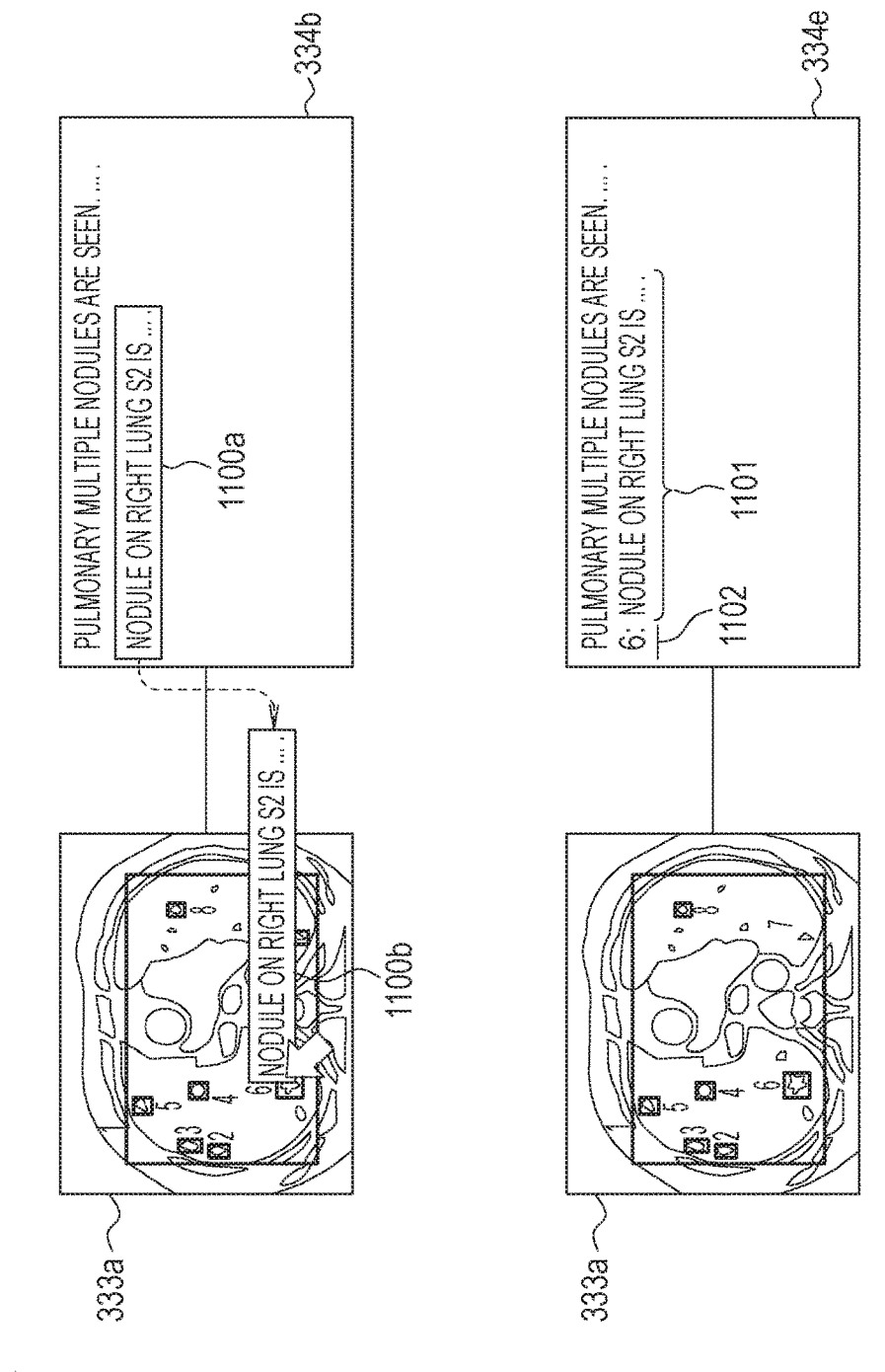

| | RADIOGRAPHIC INTERPRETATION REPORT INFORMATION | 1800 |
|---|---|---|
| | INFORMATION TYPE | REPORT IDENTIFICATION INFORMATION |
| MEDICAL INFORMATION 1 | REPORT ID | P12345-26789 |
| | RADIOGRAPHIC INTERPRETATION PHYSICIAN | OHTA HANAKO |
| | RADIOGRAPHIC INTERPRETATION DATE AND TIME | AUG 23, 2015, 11:30:28 |
| | INFORMATION TYPE | PATIENT INFORMATION |
| MEDICAL INFORMATION 2 | PATIENT NAME | SIMOMARUKO TARO |
| | PATIENT ID | P12345-26789 |
| | AGE | 75 |
| | SEX | MALE |
| | INFORMATION TYPE | EXAMINATION INFORMATION |
| MEDICAL INFORMATION 3 | EXAMINATION TYPE | CONTRAST-ENHANCED CT |
| | PART TO BE EXAMINED | THORACOABDOMINAL PART |
| | EXAMINATION DATE | AUG 23, 2015, 11:23:45 |
| | COMMENT | FOLLOW UP FOR PNEUMONIA |
| | INFORMATION TYPE | REASON FOR EXAM |
| MEDICAL INFORMATION 4 | UID | 1.3.12.2.1107.5.1.4.4853... |
| | DETAILS | FOLLOW UP FOR PNEUMONIA |
| | INFORMATION TYPE | REPRESENTATIVE IMAGE |
| MEDICAL INFORMATION 5 | UID | 1.3.12.2.1107.5.1.4.4854... |
| | ROI UID | 1.3.12.2.1107.5.1.4.5854... |
| | ROI UID | 1.3.12.2.1107.5.1.4.6854... |
| ⋮ | ⋮ | ⋮ |
| | INFORMATION TYPE | GROUP FINDINGS |
| | UID | 1.3.12.2.1107.5.1.4.1234... |
| MEDICAL INFORMATION i | FREE TEXT | PULMONARY MULTIPLE NODULES ARE SEEN...... |
| | PART | BOTH LUNGS |
| | LESION TYPE | MULTIPLE NODULES |
| | CHILD INFORMATION (UID) | 1.3.12.2.1107.5.1.4.335.26... |
| | CHILD INFORMATION (UID) | 1.3.12.2.1107.5.1.4.335.27... |
| ⋮ | ⋮ | ⋮ |
| | INFORMATION TYPE | FINDINGS |
| MEDICAL INFORMATION i+1 | UID | 1.3.12.2.1107.5.1.4.335.26... |
| | FREE TEXT | |
| | PART | RIGHT LUNG S2 |
| | LESION TYPE | NODULE |
| ⋮ | ⋮ | ⋮ |
| | INFORMATION TYPE | DIAGNOSIS |
| MEDICAL INFORMATION j | UID | 1.3.12.2.1107.5.1.4.233532... |
| | FREE TEXT | SUSPECTED PNEUMONIA. |
| | NAME OF DIAGNOSED DISEASE | LUNG CANCER |
| ⋮ | ⋮ | ⋮ |
| | INFORMATION TYPE | RECOMMENDATION |
| MEDICAL INFORMATION k | UID | 1.3.12.2.1107.5.1.4.5678... |
| | FREE TEXT | PLEASE FOLLOW UP. |
| ⋮ | ⋮ | ⋮ |
| | INFORMATION TYPE | ROI |
| MEDICAL INFORMATION l | UID | 1.3.12.2.1107.5.1.4.5854... |
| | COORDINATES | X=..., Y=... |
| | ROI NUMBER | 1 |
| ⋮ | ⋮ | ⋮ |
| | RELATIONSHIP TYPE | SUCCESSION |
| RELATIONSHIP INFORMATION 1 | SOURCE (UID) | 1.3.12.2.1107.5.1.4.0234... |
| | DESTINATION (UID) | 1.3.12.2.1107.5.1.4.1234... |
| RELATIONSHIP INFORMATION 2 | RELATIONSHIP TYPE | CAUSE/BASIS |
| | SOURCE (UID) | 1.3.12.2.1107.5.1.4.1234... |
| | DESTINATION (UID) | 1.3.12.2.1107.5.1.4.2335.2... |
| ⋮ | ⋮ | |

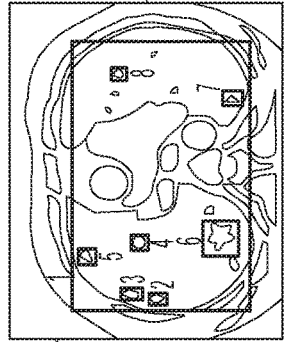
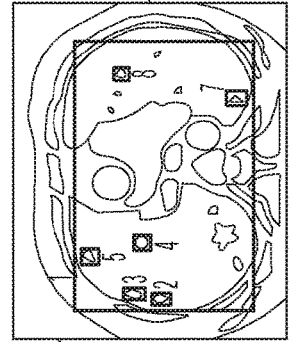
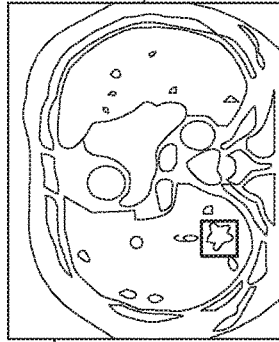
FIG. 21

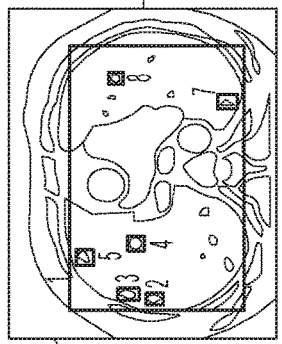
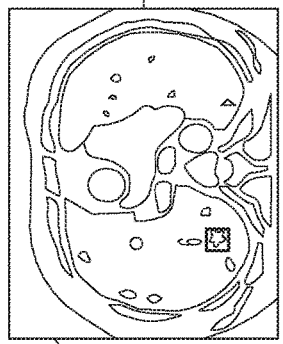
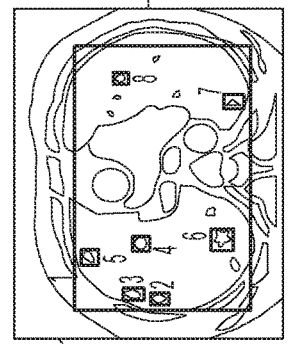
FIG. 22

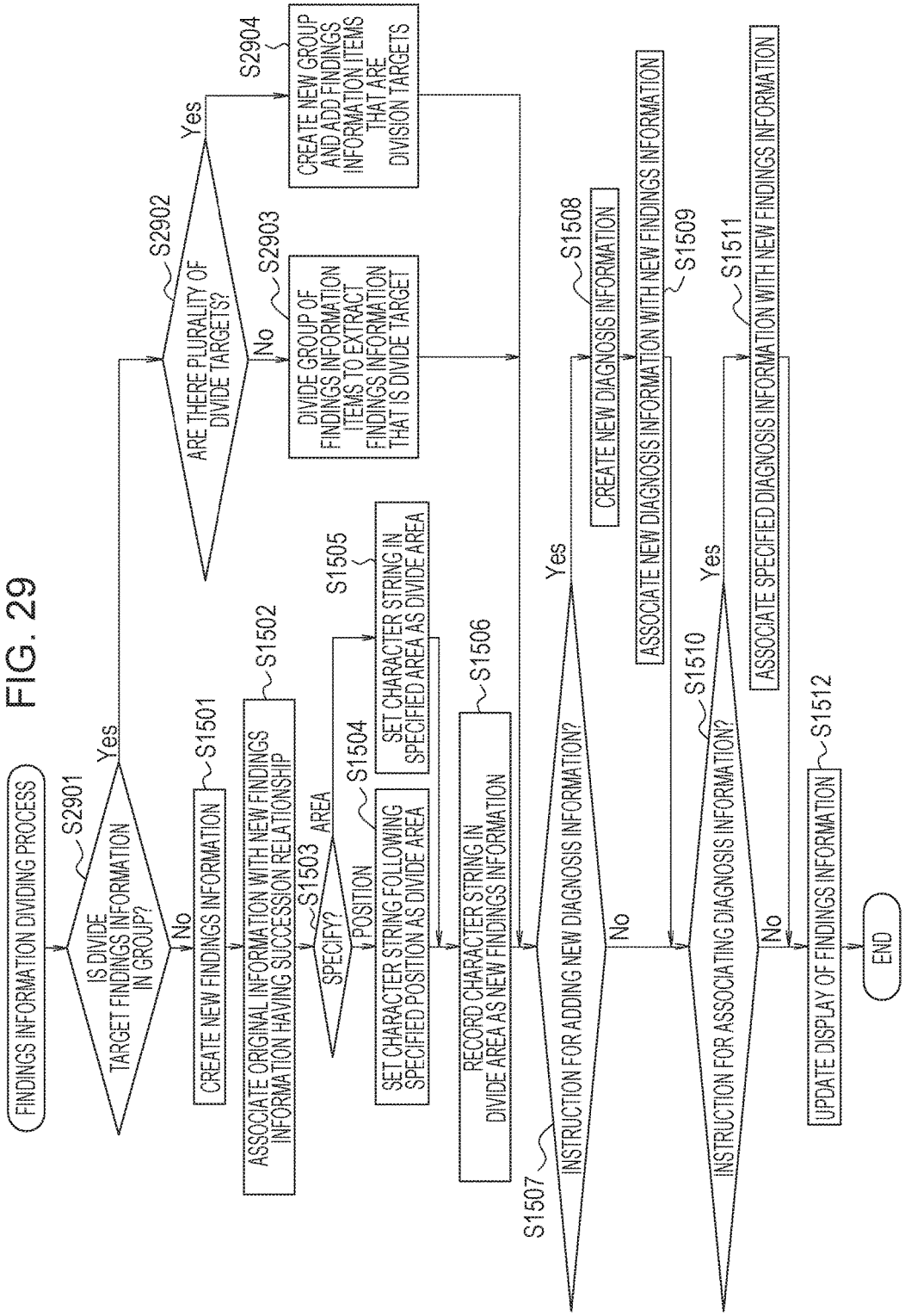

INFORMATION PROCESSING SYSTEM, INFORMATION PROCESSING METHOD, AND PROGRAM

BACKGROUND

Field of Art

The present disclosure relates to an information processing system related to medical information, an information processing method, and a program.

Description of the Related Art

In recent years, according to "Advancements in team medical service through cooperation of medical staff" (Iseihatsu. 0430 Vol. 1), "Assistance for radiographic interpretation in imaging diagnosis" has been required as a new role of a radiologist. The assistance for radiographic interpretation made by a radiologist includes detection called "preliminary radiographic interpretation" prior to radiographic interpretation made by a radiographic interpretation physician. In addition, techniques for supporting radiographic interpretation such as computer-aided detection (CADe) and computer-aided diagnosis (CADx) have been developed. By referring to findings detected in the preliminary radiographic interpretation or CADe, a radiographic interpretation physician makes radiographic interpretation, makes an imaging diagnosis, and creates a radiographic interpretation report.

in particular, in creating a radiographic interpretation report for follow-up, it is important to assess changes of lesions over time. For example, lesions, such as multiple lesions, which have been considered as a group, may be divided during treatment as in the case where a single pulmonary nodule of multiple pulmonary nodules that have been suspected to be attributed to pneumonia is changed to be attributed to suspected lung cancer. In such a case, a physician needs to follow the changes of lesions over time.

As technique for supporting the creation of a radiographic interpretation report for follow-up, Japanese Patent Laid-Open No. 2015-179319 discloses a technique for receiving lesion information and. receiving report information regarding a lesion to be registered in association with the name of a diagnosed disease and for displaying the lesion information and the report information in association with each other. In addition, Japanese Patent Laid-Open No. 2013-157034 discloses a technique for associating text in a radiographic interpretation report with other information, for example, associating a character string in findings with an annotation in an image. Furthermore, Japanese Patent Laid-Open No. 2002-116910 discloses a technique for dividing a node of a tree structure on the basis of key input.

SUMMARY

The present disclosure provides an information processing system including one or more processors; a receiving unit configured to receive a divide instruction for dividing first medical information corresponding to a first display image representing a target region to extract a part of details of the first medical information if the first medical information and the first display image are displayed in association with each other on a display unit; and a display processing unit configured to, if the divide instruction has been received, display the part of details on the display unit newly as second medical information that is different from the first medical information and to display a second display image representing a target region corresponding to the part of details in association with the second medical information on the display unit.

Further features will become apparent from the following description of exemplary embodiments with reference to the attached drawings.

BRIEF DESCRIPTION OF THE DRAWINGS

FIGS. 3A and 3B illustrate examples displayed on displays.

FIG. 5 illustrates an example of radiographic interpretation report information.

FIGS. 6A and 6B illustrate examples of report screens displayed when succession-duplicating is performed.

FIGS. 7A and 7B illustrate examples of report screens displayed when findings information is divided.

FIG. 10 illustrates an example of a report screen displayed during time-series display.

FIG. 11 illustrates a user operation.

FIG. 18 illustrates an example of radiographic interpretation report information according to a second embodiment.

FIGS. 19A and 19B illustrate examples of report screens.

FIGS. 20A and 20B illustrate examples of report screens when findings information is divided.

FIG. 21 illustrates an example of findings information and the like when findings information is divided.

FIG. 22 illustrates processing for combining findings information and representative images.

FIG. 29 is a flowchart illustrating a findings information dividing process.

DESCRIPTION OF THE EMBODIMENTS

First Embodiment

As described in the BACKGROUND section, during follow-up, the group of lesions may be changed in some cases. In these cases, it is desirable to manage medical information such that changes in lesions can be followed over time.

The present disclosure has been made in view of the above-described issue and provides a technique for displaying medical information such that changes in lesions can be followed over time even if the group of lesions has been changed.

Now, embodiments will be described below with reference to the drawings.

Figure 1:
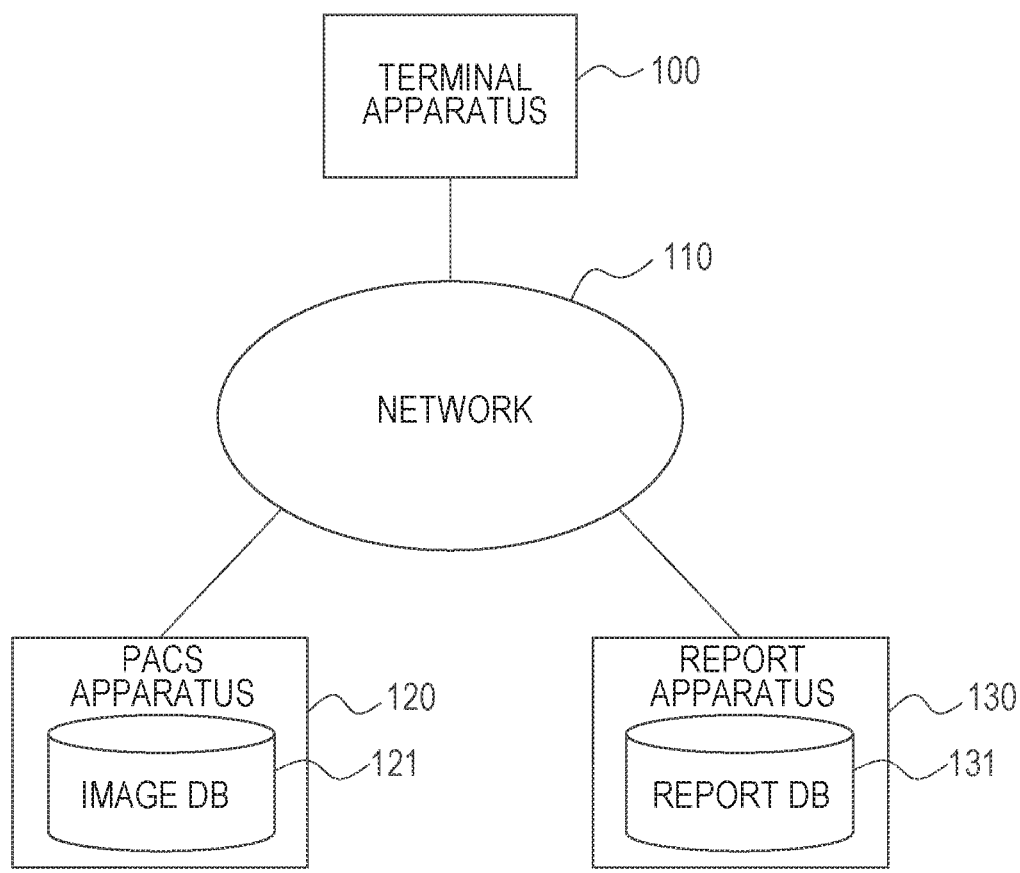
FIG. 1 illustrates a medical information display system.

FIG. 1 illustrates a medical information display system according to a first embodiment. This embodiment describes an exemplary case in which the medical information display system displays a radiographic interpretation report of a medical imaging diagnosis as medical information. However, the medical information display system may display any medical information, and the type thereof is not limited to the specific medical information illustrated in this embodiment. For example, the medical information display system may display a report of other diagnosis.

The medical information display system includes a terminal apparatus 100, a picture archiving and communication system (PACS) apparatus 120, and a report apparatus 130. Here, the terminal apparatus 100 is an example of an information processing apparatus and an information processing system. The PACS apparatus 120 is a server apparatus that includes an image database (DB) 121 and that provides a function of storing and reading examination images through a network 110. The image DB 121 stores patient information, examination information, and examination images in association with one another. The patient information is information regarding patients. The examination information is information regarding examinations. The examination image is an image in accordance with the Digital Imaging and Communications in Medicine (DICOM) standard, captured by using computed tomography (CT) or magnetic resonance imaging (MRI). The examination image is an example of medical information.

The report apparatus 130 is a server that includes a report DB 131 and that provides a function of storing and reading radiographic interpretation report information through the network 110. The report DB 131 stores the radiographic interpretation report information. The radiographic interpretation report information indicates a report of an examination image and includes different types of a plurality of medical information items. The radiographic interpretation report information includes findings on the examination image, a diagnosis based on the findings, a recommended examination based on the diagnosis, and the like.

The terminal apparatus 100 reads radiographic interpretation report information of an examination that has been specified as a display target from the report apparatus 130 and displays the read radiographic interpretation report information. In accordance with a specified representative image, the terminal apparatus 100 also reads a corresponding examination image from the PACS apparatus 120 and displays the read examination image.

Figure 2:
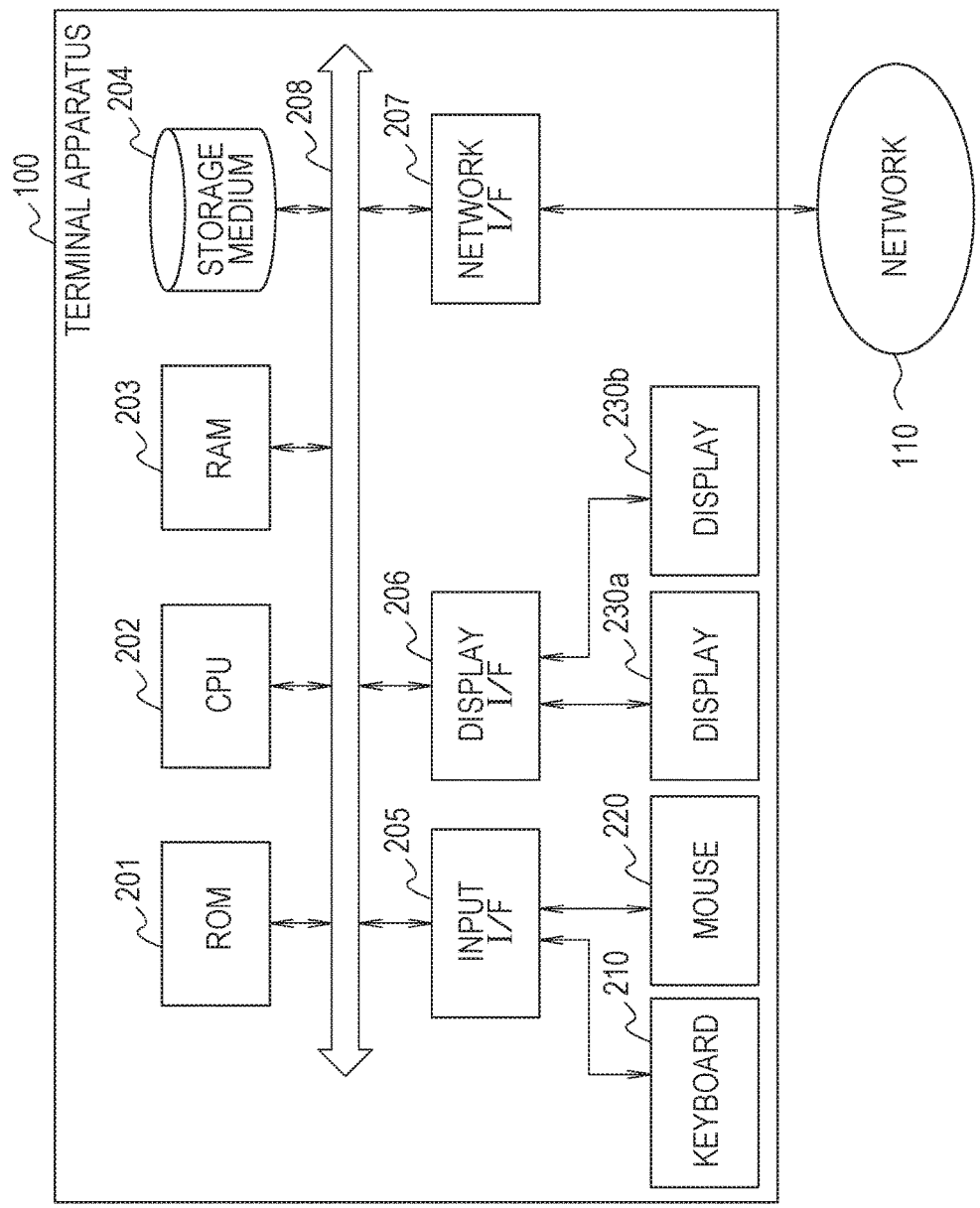
FIG. 2 illustrates a hardware configuration of a terminal apparatus.

FIG. 2 illustrates a hardware configuration of the terminal apparatus 100. A storage medium 204 is, for example, a hard disk drive (HDD) that stores operating systems (OS), processing programs, and various information items. A read only memory (ROM) 201 stores a program for starting an OS such as a basic input output system (BIOS). A central processing unit (CPU) 202 performs arithmetic processing when executing various programs. A random access memory (RAM) 203 temporarily stores various information items when the CPU 202 executes a program. Note that the functions and processing of the terminal apparatus 100, which will be described later, are realized by the CPU 202 reading and executing programs stored in the ROM 201 or the storage medium 204.

An input interface (I/F) 205 is a communication interface such as a universal serial bus (USB) for connecting input devices such as a keyboard 210 and a mouse 220. A display I/F 206 is an interface such as a graphic board for displaying screens on displays 230a and 230b. A network I/F 207 is an interface complying to, for example, the Institute of Electrical and Electronics Engineers (IEEE) 802.3ab standard for performing communication through the network 110. An internal bus 208 is for each block performing communication.

Figure 3A:
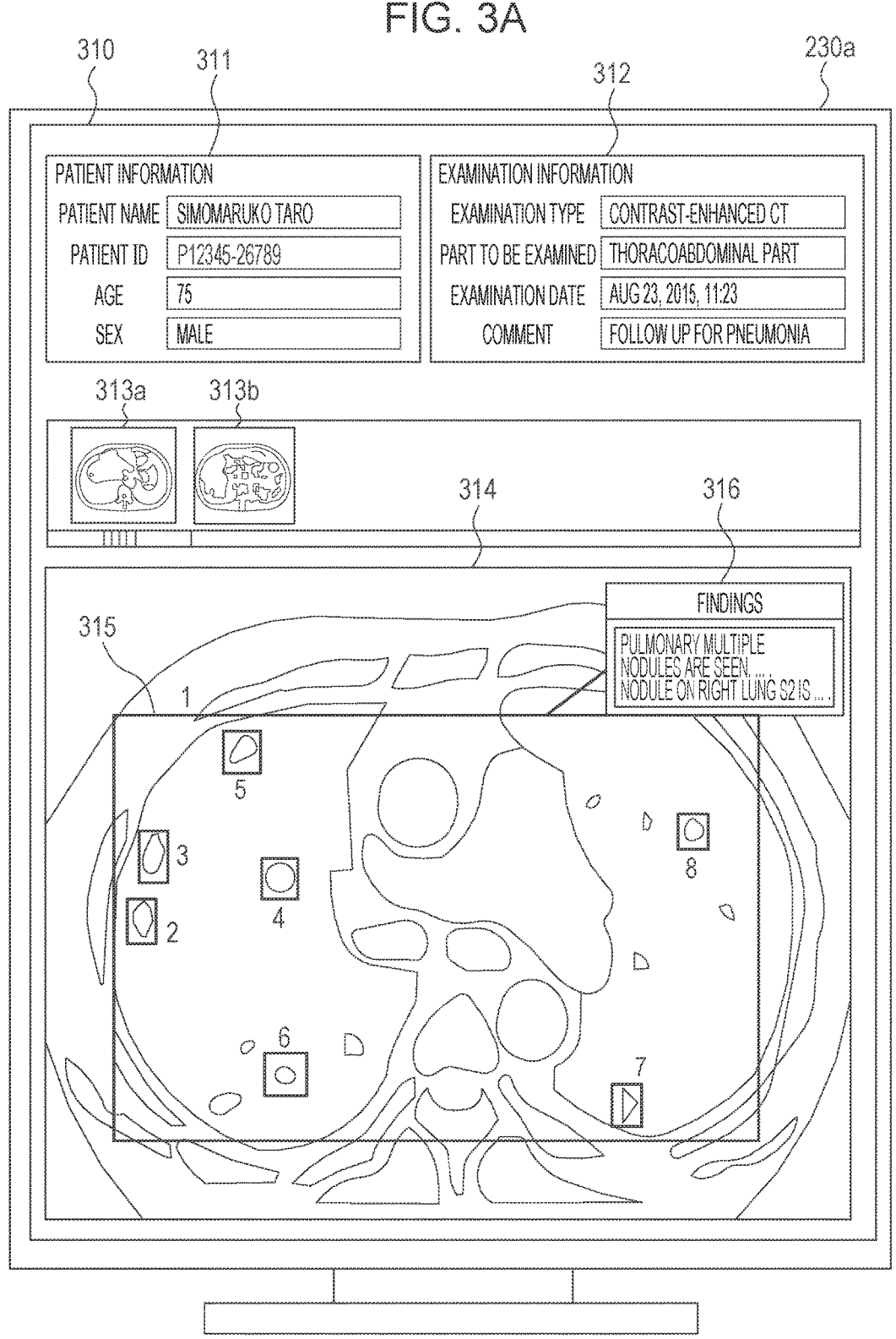

FIGS. 3A and 3B respectively illustrate examples displayed on the displays 230a and 230b. In this embodiment, a viewer screen 310 is displayed on the display 230a, and a report screen 320 is displayed on the display 230b. The viewer screen 310 is a screen for displaying an examination image captured during a patient's examination that is a display target. The report screen 320 is a screen for displaying radiographic interpretation report information of the patient's examination that is a display target.

On the viewer screen 310, a region 311 is for displaying patient information. The patient information Includes patient name, patient identification (ID), patient age, patient sex, and the like. A region 312 is for displaying examination information. The examination information includes examination type, part to be examined, examination date, comment, and the like.

A region 314 is for displaying the examination image. In this region, for example, it is possible to move a slice position to be displayed, to change conditions for image display such as window level (WL)/window width (WW), and to display a region of interest (ROI) and other shapes. The ROI is an example of a target region and is a region on which a physician is to be focused, such as a part related to a lesion. Images 313a and 313b are representative images of examination images captured during the same examination. In response to a user selection operation such as a drag-and-drop operation on the representative image 313a or 313b, the corresponding image can be displayed in the region 314. A shape 315 is added to the image and is used to express the position of a lesion or the like. The shape is not limited to a rectangle and may be an ellipse, a circle, a polygon, a free closed curve, a triangle, straight line, an arrow, and the like.

In an input frame 316, findings text associated with the shape 315 or a slice image are input and displayed. The input frame 316 may be displayed as soon as the slice image is displayed, may be switched to be displayed and hidden from being displayed in response to an operation, or may be automatically displayed if the slice image is displayed for a predetermined period.

On the report screen 320, a region 321 is for displaying the patient information. A region 322 is for displaying the examination information. A past report region 330 is for displaying radiographic interpretation report information regarding the patient of the currently selected examination, the information having been obtained prior to the creation of the radiographic interpretation report information of the examination that is the display target. In addition, the radiographic interpretation report information obtained prior to the creation of the radiographic interpretation report information of the examination that is the display target is referred to as past radiographic interpretation report information. Upon starting the terminal apparatus 100, radiographic interpretation report information of an examination that has been conducted immediately before the examination that is selected as the display target is displayed in the past report region 330. A current report region 340 is for displaying the radiographic interpretation report information of the examination that is the display target, that is, the radiographic interpretation report information that is currently being created. Note that the radiographic interpretation report information of the examination that is the display target is referred to as current radiographic Interpretation report information. Editing of the past report region 330, such as writing and deleting text, is not allowed, whereas editing the current report region 340 is allowed.

A control 331 is used for selecting a past examination. Upon clicking the control 331 with the mouse, a list of past examinations is displayed so that a given examination can be selected. A display frame 332*a* is for displaying the reasons for exams of past examinations one by one. Information displayed in the display frame 332*a* may be produced by a physician who commissions an examination on a system for commissioning the examination or by a radiographic interpretation physician when creating the past, radiographic interpretation report information. Alternatively, the information displayed in the display frame 332*a* may be extracted and generated through a linguistic analysis from free text stated as the reason for exam.

A medical display image 333*a* is generated from a representative image illustrated in the past radiographic interpretation report information. The representative image is a slice image indicating features of findings and is set, for example, in accordance with a user operation. The medical display image is an image obtained by superimposing, on the representative image, one or more images representing ROIs indicated by findings information. Findings information 334*a* corresponds to the representative image. The findings information is medical information indicating findings detected in the representative image. The findings information includes a fact or objective information found in the image. The findings information may include, not only findings of the radiographic interpretation physician by observing the image, but also preliminary radiographic interpretation findings of a radiologist and imaging analysis findings made by CADe or the like. In such cases, the display format is changed (not illustrated) in such a manner that it may be distinguished who or what has made the findings.

In addition, the medical display image 333*a* and the findings information 334*a* are linked to each other by a line representing the correspondence relationship between the information items. In the above manner, a display processing unit 411 (see FIG. 4) displays the line linking the medical display image 333*a* to the findings information 334*a*, thereby displaying the medical display image 333*a* and the findings information 334*a* in association with each other. Note that the display processing unit 411 may display the association between the information items in any manner as long as the association therebetween is recognizable, and the display format is not limited to the specific example in this embodiment. As another example for displaying the association, a plurality of information items to be displayed in association with each other may be displayed in the same color or may be displayed within the same display frame, for example.

Diagnosis information 33.5*a* is based on the findings information 334*a*. The diagnosis information is subjective information on a disease or the like determined. based on the findings. The diagnosis information 335*a* is linked to the findings information 334*a* with an arrow indicating the cause or basis. The findings information and the diagnosis information may have a one-to-one relationship, a one-to-many relationship, a many-to-one relationship, or a many-to-many relationship. Recommendation information 336*a* is based on the diagnosis information 335*a*. The recommendation information is information on an examination or the like recommended in accordance with the details of the diagnosis. The recommendation information 336*a* is linked to the diagnosis information. 335*a* with an arrow indicating the cause or basis. The diagnosis information and the recommendation information may also have a one-to-one relationship, a one-to-many relationship, a many-to-one relationship, or a many-to-many relationship.

A display frame 332*b* is for displaying the reason for exam of the examination (current examination) that is the display target in a manner similar to that in the display frame 332*a*. in the past report region 330. In addition, a medical display image 333*b* is generated from a representative image illustrated in the current radiographic interpretation report information in a manner similar to that in the medical display image 333*a* in the past report region 330. Findings information 334*b*, diagnosis information 335*b*, and recommendation information 336*b* are each related to the current radiographic interpretation report information. The representative images corresponding to the medical display images, the findings information, the diagnosis information, and the recommendation information illustrated in FIGS. 3A and 3B are different types of medical information. For example, a representative image is medical information with an information type of "representative image", and the findings information is medical information with an information type of "findings information".

Although not illustrated, the reason for exam may have a correspondence relationship with findings information, diagnosis information, and recommendation information, in which case the corresponding information is highlighted by selecting the reason for exam. In addition, the findings according to the past report and the findings according to the current report can have a chronological relationship (hereinafter referred to as a "succession relationship") in which case the corresponding information is highlighted as in the above relationship with the reason for exam.

A button 351 is for quitting without saving the created report, a button 352 is for quitting by saving the report temporarily, and a button 353 is for quitting by saving the report permanently. A button 350 is for switching the screen to a screen (hereinafter referred to as "time-series display") for displaying specified findings information items arranged in the time-series order. The time-series display will be described later with reference to FIG. 10. Note that the type of displayed information, the display layout, and the method for displaying the information or relationship are not Limited to the examples herein.

Figure 4:
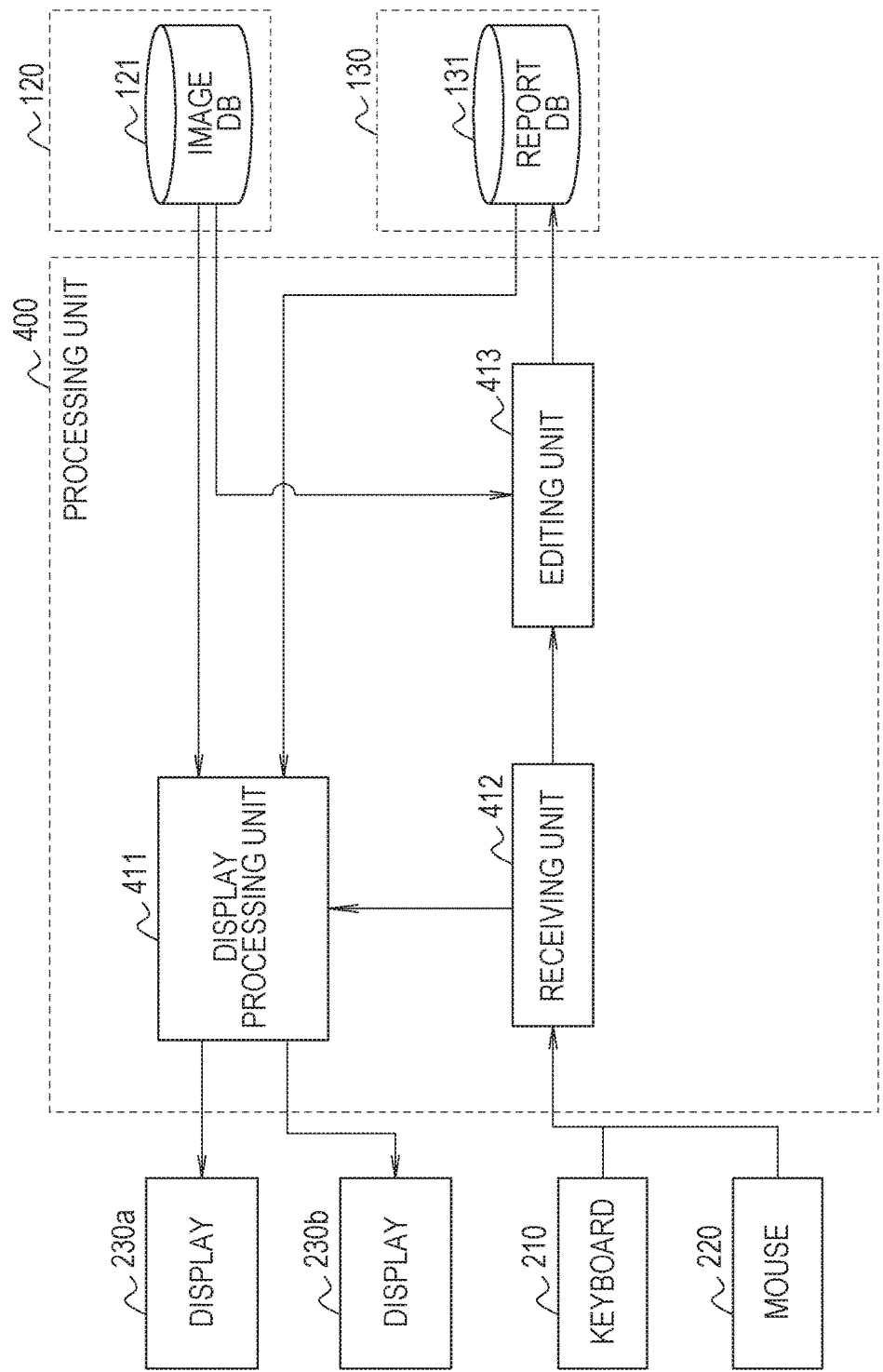
FIG. 4 illustrates a software configuration of the terminal apparatus.

FIG. 4 illustrates a software configuration of the terminal apparatus 100. The display processing unit 411 in a processing unit 400 of the terminal apparatus 100 reads patient information, examination information, and an examination image of an examination that is a display target from the image DB 121 in the PACS apparatus 120, generates the viewer screen 310, and displays the viewer screen 310 on the display 230*a*. The display processing unit 411 also reads radiographic interpretation report information from the report DB 131 in the report apparatus 130, generates the report screen 320, and displays the report screen 320 on the display 230*b*. The display processing unit 411 also changes conditions for image display, selects a past examination, and switches the screen to time-series display, for example.

Although not illustrated in FIG. 4, image data is read from the image DB 121 through the network 110, and the radiographic interpretation report information is read from the report DB 131 through the network 110.

FIG. 5 illustrates an example of radiographic interpretation report information. Radiographic interpretation report information. 500 includes a plurality of medical information items and a plurality of relationship information items. That, is, the plurality of medical information items included in the radiographic interpretation report information 500 are managed as information items that are associated with each other by being included in the same radiographic interpretation report information 500. Note that the CPU 202 of the terminal apparatus 100 reads the radiographic interpretation report information 500 from the report apparatus 130 and records the radiographic interpretation report information 500 in a memory unit, such as the RAM 203, of the terminal apparatus 100 when the terminal apparatus 100 displays a viewer screen and a report screen.

The medical information is information that is referred to in the medical field. Each medical information item includes "information type" and "attribute information". In this embodiment, as the information type of medical information, any one of "report identification information", "patient information", "examination information", "reason for exam", "representative image", "findings", "diagnosis", "recommendation", and "ROI" is set. Note that the information types of medical information are not limited to those in this embodiment. Hereinafter, medical information items whose information types are "report identification information", "patient information", and "examination. information" are referred to as "report identification information", "patient information", and "examination information", respectively, as necessary. In addition, medical information items whose information types are "reason for exam", "representative image", "findings", "diagnosis", "recommendation", and "ROI" are referred to as "reason for exam information", "representative image", "findings information", "diagnosis information", "recommendation information", and "ROI information", respectively, as necessary.

The relationship information indicates a specific relationship between medical information items. Each relationship information item in this embodiment includes "relationship type" and "attribute information". In this embodiment, as the relationship type of the relationship information, any one of "correspondence", "cause/basis", and "succession" is set. Note that the relationship types of the relationship information are not limited to those in this embodiment.

The report identification information includes attribute information such as report ID, name of radiograph interpretation physician, or imaging date and time. In addition, the patient information includes attribute information such as patient name, patient ID, patient age, and patient sex. In addition, the examination information includes attribute information such as examination type, part to be examined, examination date, and comment. The representative image includes a unique identifier (UID) for uniquely identifying an examination image as a representative image and ROI UIDs for identifying ROI information related to ROIs added to the representative image. The representative image may further include information on conditions for image display in order to reproduce an image.

The reason for exam information includes attribute information such as UID and details (text). The findings information includes attribute information such as UID, free text on findings, name of part, and lesion type. Here, the name of part and the lesion type may be extracted from the free text through a linguistic analysis or may be input by a user. The diagnosis information includes attribute information such as UID, free text, and name of diagnosed disease. The recommendation information includes attribute information such as UID and free text. The ROI information includes attribute information such as UID, coordinates, and ROI number. Note that ROIs have a parent-children relationship based on an inclusion relationship. If child ROI information is created, a character string "ROI number:" corresponding to the ROI information is added to findings information corresponding to its parent ROI information.

The relationship information includes attribute information such as UIDs of a source and a destination. As each of the UIDs of the source and the destination, any of UIDs of the reason for exam information, representative image, findings information, diagnosis information, recommendation information, and ROI information is input. As described above, the radiographic interpretation report information 500 includes the plurality of medical information items and is for determining the relationship between the plurality of medical information items. Note that the data structure of information for determining the relationship between the plurality of medical information items is not limited to the data structure of the radiographic interpretation report information 500.

Referring back to FIG. 4, a receiving unit 412 receives an instruction in accordance with a user operation. For example, the receiving unit 412 receives an instruction for specifying medical information with at least one information type of "reason for exam", "representative image", "findings", "diagnosis", and "recommendation" described in the radiographic interpretation report information, the instruction corresponding to a predetermined input operation on the report screen 320. For example, the input operation is, but not limited to, a left click with the mouse 220 on information or an input operation with an arrow key or arrow keys of the keyboard 210. In addition, the receiving unit 412 receives an instruction for editing the radiographic interpretation report information, the instruction corresponding to an operation on the keyboard 210 or with the mouse 220. The editing here means creation of medical information of "ROI" or "findings", pasting of a representative image, creation of an item such as "reason for exam", "diagnosis", or "recommendation", text editing of an item, adding, changing, or deleting association between items, deleting of an item, dividing of medical information of "findings", or the like.

An editing unit 413 edits the radiographic interpretation report information 500 in accordance with the instruction received by the receiving unit 412 and further, in accordance with the edit result, updates the radiographic interpretation report information 500 in the report DB 131. For example, if a findings information item is divided into two findings information items, the editing unit 413 edits the radiographic interpretation report information 500 in such a manner that each findings information stem corresponds to a representative image. Note that detailed processes performed by the editing unit 413 will be described later.

Figure 6A:
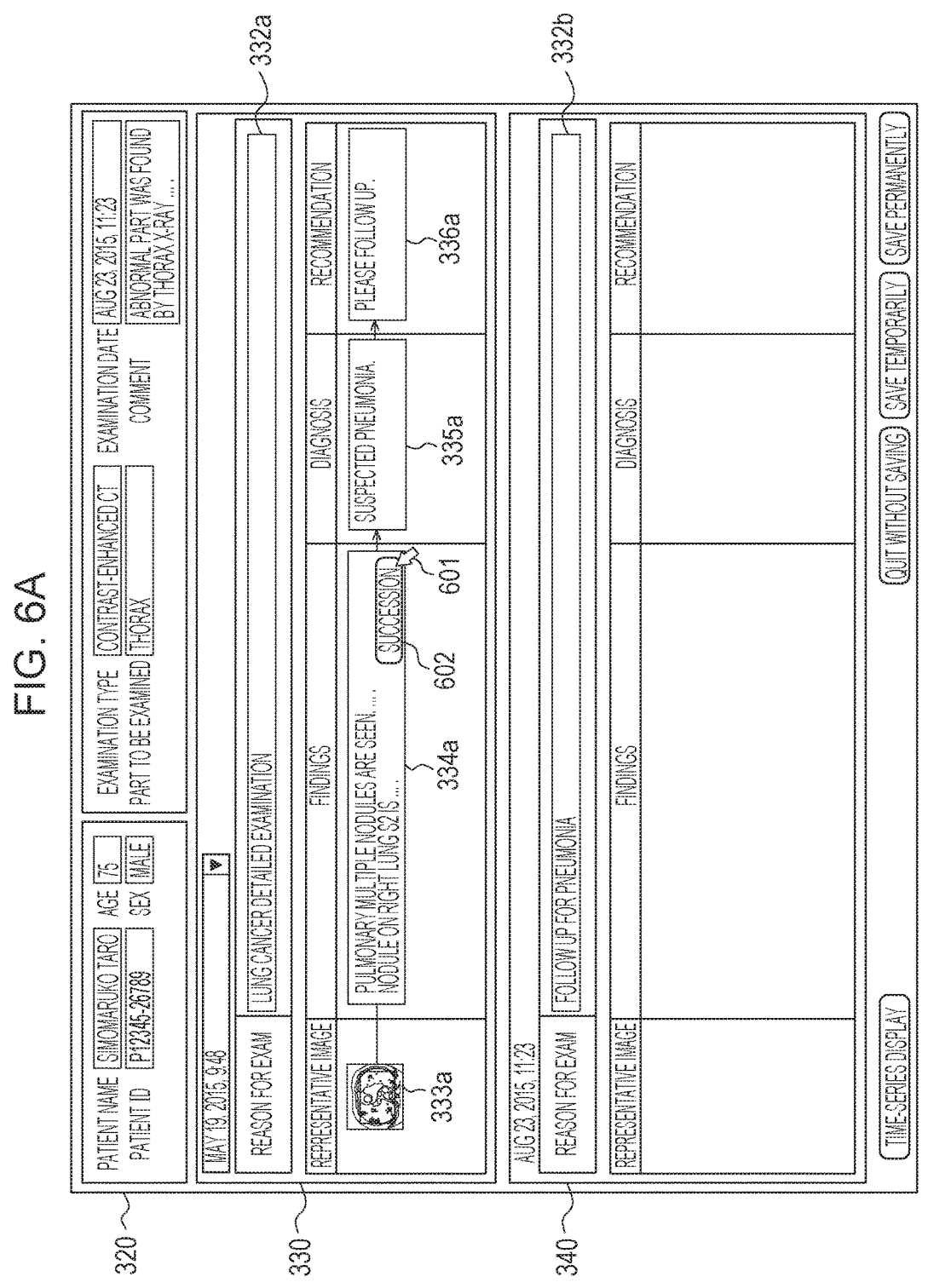
Figure 6B:
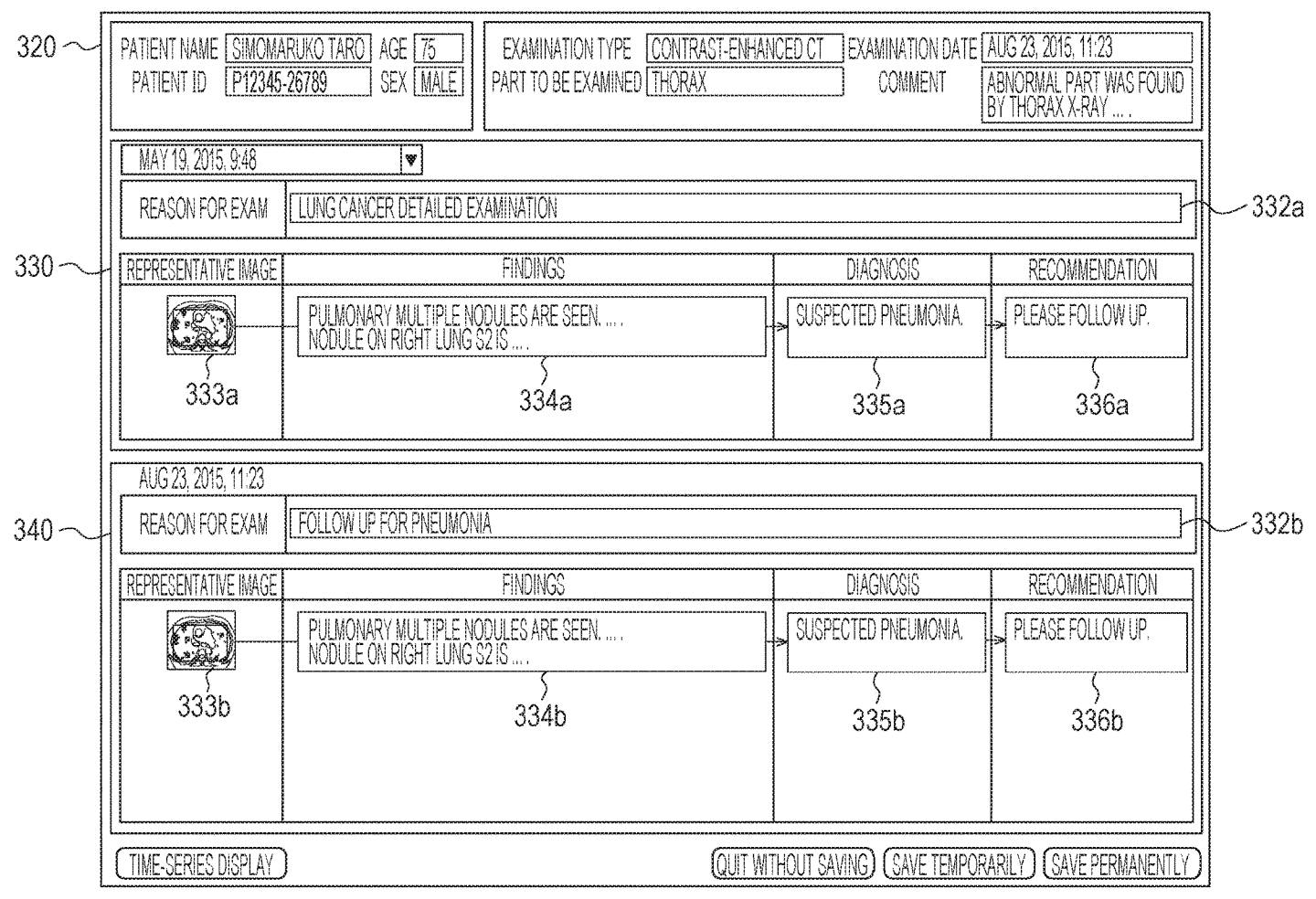

FIGS. 6A and 6B each illustrate the report screen 320 displayed at the time of succession-duplicating. Here, the succession-duplicating means processing for creating new findings information having a chronological relationship with past findings information by duplicating the past findings information. FIG. 6A illustrates the report screen 320 displayed at the time of creating a new current report. The current examination date and time is "Aug. 23, 2015, 11:23", and the past examination date and time is "May 19, 2015, 9:48". The purpose of the past examination is "lung cancer detailed examination" as illustrated in the display frame 332a. Multiple nodules are seen in the medical display image 333a according to the findings information 334a, the suspected disease is pneumonia, and follow-up is recommended as indicated by the diagnosis information 335a and the recommendation information 336a.

In accordance with the past examination, the reason for exam of the current examination is "follow up for pneumonia" as illustrated in the display frame 332b. Then, with the mouse (a pointer 601 is a pointer of the mouse), a user such as a physician selects the findings information. 334a of the past examination indicating multiple nodules and clicks a button 602 for succession displayed on mouseover. In response, the findings information 334a is succession-duplicated to the current report. Succession-duplicated information is information to which the succession relationship is added.

FIG. 6B illustrates an example of a display screen after succession-duplication. The medical display image 333a and the medical display image 333b, the findings information 334a and the findings information 334b, the diagnosis information 335a and the diagnosis information 335b, and the recommendation information 336a and the recommendation information 336b have a succession relationship. Here, in order to paste the medical display image 333b, it is necessary to determine the series of a current image corresponding to the past image and to position the images. The series is determined by matching of DICOM information, but specifying the series is not limited to the matching of DICOM information, and the images are positioned by a known method for minimizing the difference between three-dimensional image information items of the series of the past image and the series of the current image, but positioning of the images is not limited to this method.

FIGS. 7A and 7B each illustrate the report screen 320 when the findings information is divided. FIG. 7A illustrates the report screen 320 displayed when the user inputs an instruction for dividing the findings information. Information 700a is specified by the user and is a character string in the findings information 334b. That is, the information 700a corresponds to a part of the details of the findings information 334b. If the user performs an operation for associating the information 700a with diagnosis information 335c, the receiving unit 412 receives a divide instruction for dividing the findings information 334b to extract the information 700a. Upon receiving the divide instruction, the display processing unit 411 displays the information 700a as new findings information and deletes the information 700a from the findings information 334b that is displayed.

FIG. 7B illustrates the report screen 320 after a process in accordance with the divide instruction. On the report screen 320 illustrated in FIG. 7B, findings information 334c and findings information. 334d are obtained by dividing the findings information 334b in accordance with the divide instruction. In addition, in accordance with the division of findings information, a medical display image 333c and a medical display image 333d are also obtained by dividing the corresponding medical display image 333b.

Note that the associating operation is, for example, an operation (700b) for selecting the information 700a and dragging-and-dropping the information 700a on the diagnosis information 335c. Although not illustrated, upon pushing a tab key while the information 700a is selected, the receiving unit 412 receives an addition instruction for adding new diagnosis information to the information 700a. The new diagnosis information is different from the diagnosis information 335b associated with the findings information 334b. Accordingly, this operation is an operation for setting the information 700a, which is a part of the findings information 334b, as new findings information. In addition, pushing of a "Ctrl" key and an "Enter" key together while a cursor for character input is within a character string in the findings information 334b is an operation for dividing the findings information 334b to extract a character string behind the cursor position. Alternatively, the divide instruction may be input with a button, menu, or the like.

Figure 8:
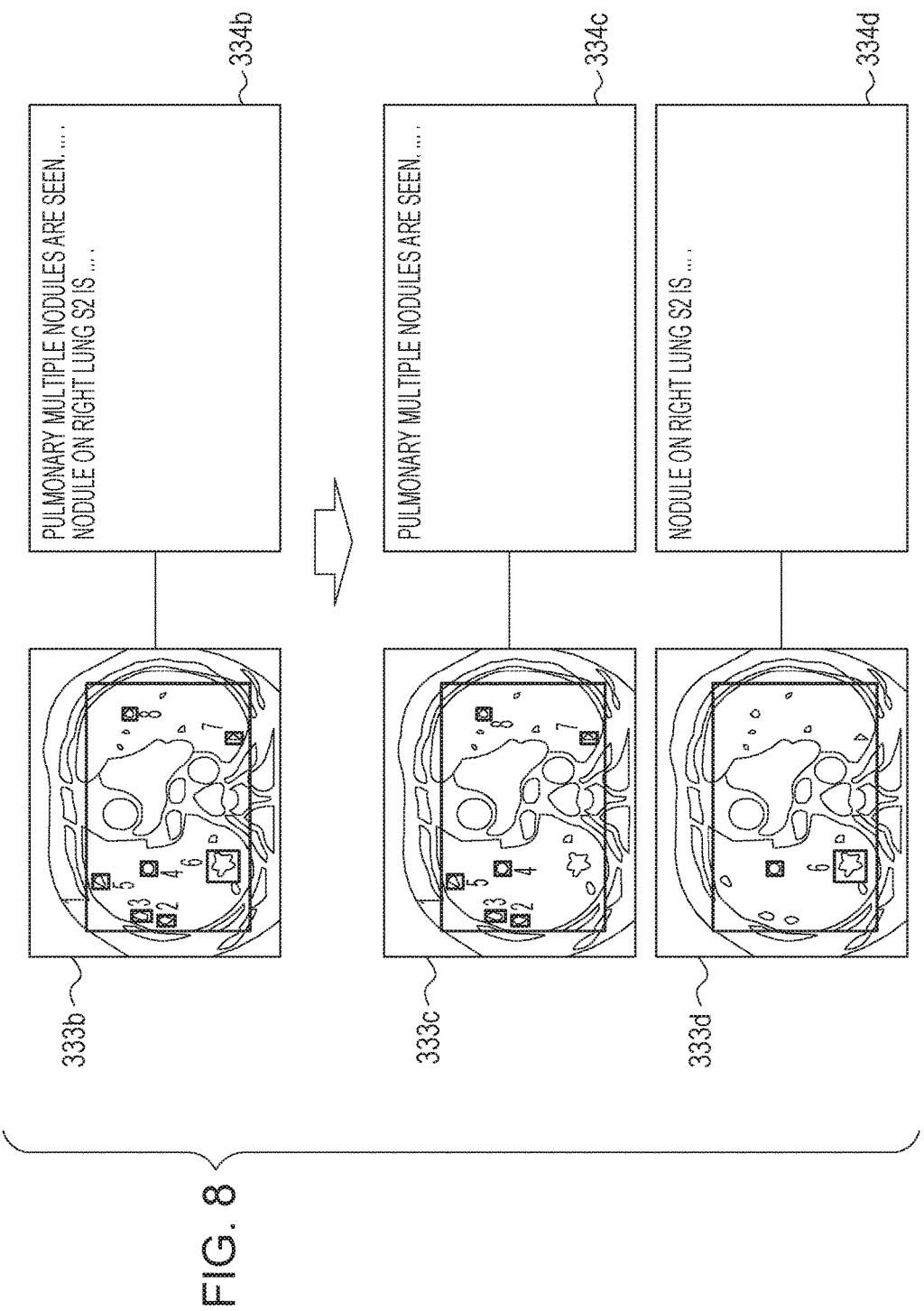
FIG. 8 illustrates an example of findings information and the like displayed when findings information is divided.

FIG. 8 illustrates medical display images displayed before and after dividing findings information. If a plurality of ROI information items are associated with findings information, as medical display images, the display processing unit 411 displays an image in which a plurality of ROI numbers and ROI display frames related to the respective ROI information items are superimposed on an examination image (captured image) set as a representative image. Here, each ROI number and ROI display frame is an example of a region image representing a target region. In addition, the ROI number is an image representing identification information of a ROI as a target region and is an example of a region image representing a target region. Hereinafter, the display frame and the ROI number are each referred to as a region image as necessary.

For example, in the radiographic interpretation report information 500, it is assumed that eight ROI information items corresponding to ROI numbers 1 to 8 are associated with the findings information 334a associated with the representative image. In this case, as illustrated in FIG. 8, the display processing unit 411 displays an image in which the ROI numbers and display frames corresponding to the respective eight ROIs are superimposed on the representative image as the medical display image 333b.

Note that, for example, if ROIs corresponding to ROI numbers 2 to 8 are specified as child ROIs of a ROI corresponding to ROI number 1, as illustrated in FIG. 8, the medical display image 333a is an image in which display frames of ROI numbers 2 to 8 are arranged within the display frame of ROI number 1. In the above manner, the display processing unit 411 depicts the medical display image on the basis of the captured image and the target regions.

If the findings information 334b is divided into the findings information 334c and the findings information 334d, on the basis of the correspondence relationship between a dividing-related character string and ROIs, the medical display image 333c and the medical display image 333d that are respectively corresponding to the findings information 334c and the findings information 334d are generated and displayed. The medical display image 333c displayed in this case is a slice image (examination image) on which region images corresponding to ROI numbers 1 to 5, 7, and 8 are superimposed, and the medical display image 333d is a slice image (examination image) on which region images corresponding to ROI number 6 are superimposed. Note that the slice images as the medical display images 333c and 333d are the same image.

Figure 9:
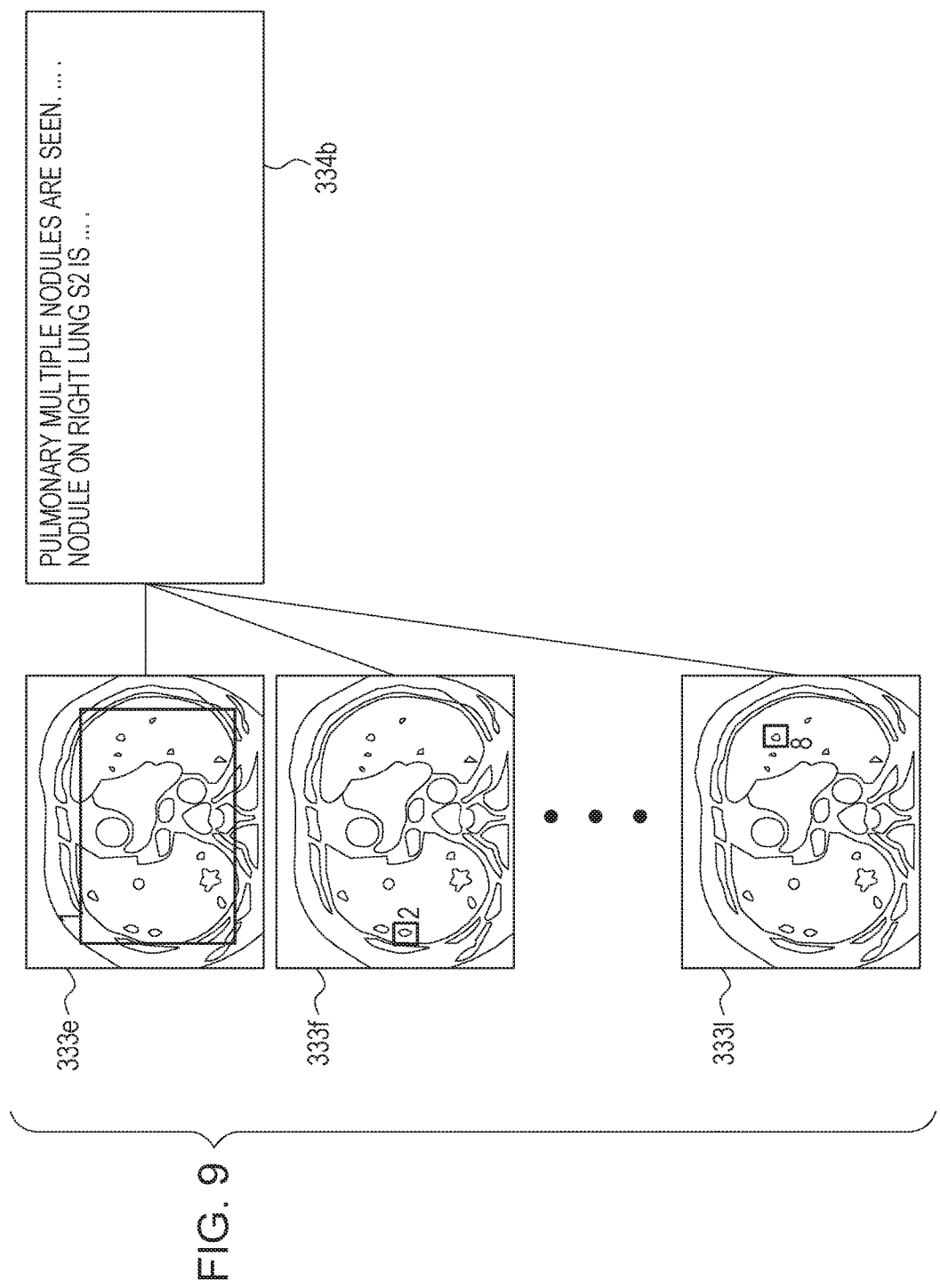
FIG. 9 illustrates an example of findings information and representative images.

As another example, as illustrated in FIG. 9, if a plurality of ROI information items are associated with a single findings information item, the display processing unit 411 may display a plurality of medical display images each corresponding to ROI information item in association with the single findings information item. With the findings information 334b corresponding to eight ROI information items, as illustrated in FIG. 9, eight medical display images 333e to 333l are displayed in association with the single findings information 334b. Here, the medical display images 333e to 333l are slice images on which region images corresponding to ROI numbers 1 to 8, respectively, are superimposed. As another example, region images corresponding to all of the ROIs may be superimposed on each of the plurality of medical display images 333e to 333l, and region images corresponding to a ROI or ROIs corresponding to the findings information and region images corresponding to a ROI or ROIs not corresponding to the findings information may be displayed in different display formats. Accordingly, as a display method in different display formats by which the region images corresponding to a ROI or ROIs corresponding to the findings information may be distinguished from the region images corresponding to a ROI or ROIs not corresponding to the findings information, for example, methods for differentiating the thicknesses or colors of lines in ROI numbers or display frames may be employed.

Figure 10:
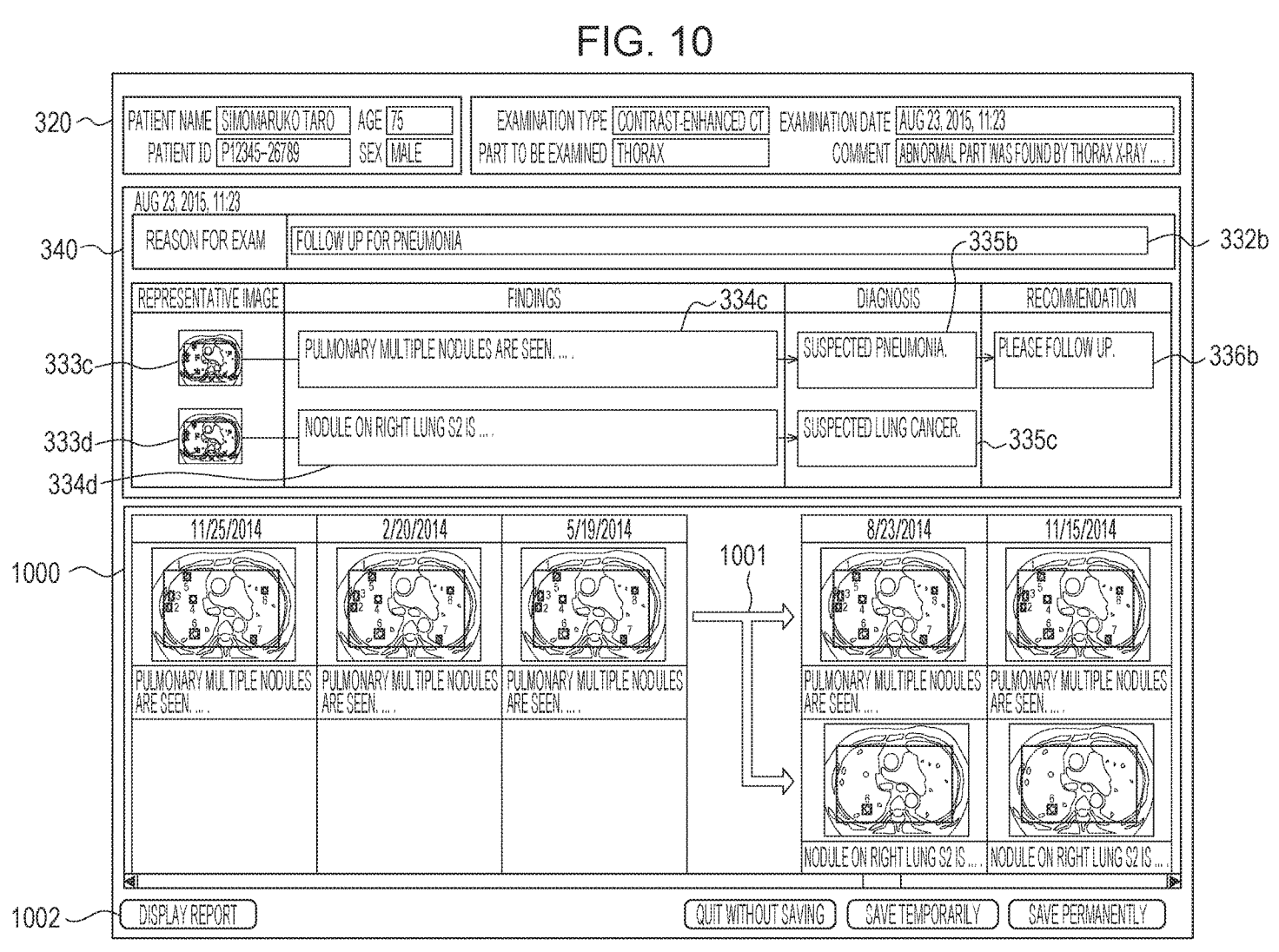

FIG. 10 illustrates an example of the report screen. 320 displayed during time-series display. On this screen, medical display images corresponding to findings information of five examinations on "Nov. 25, 2014", "Feb. 20, 2015", "May 19, 2015", "Aug. 23, 2015", and "Nov. 15, 2015" are displayed in the time-series order in a display region 1000. Here, an arrow 1001 indicates that findings information was divided at the time corresponding to the display position. A button 1002 for display is a button for terminating the time-series display by clicking to return to a screen for displaying and inputting a report.

FIG. 11 illustrates a user operation for associating a divide target, which is a part (character string) of details of the findings information, with ROI information. The user drag-and-drops (1100b) a part 1100a of details of the findings information 334b in a display frame of a desired ROI in the medical display image 333a. Upon performing the drag-and-drop operation, the terminal apparatus 100 associates toe part 1100a. with the ROI information (ROI information corresponding to ROI number 6 in the example of FIG. 11). Here, the association means recording a plurality of target information items in association with each other. In this embodiment, the editing unit 413 adds, to the radiographic interpretation report information 500, information for associating the part of details with the ROI number.

In addition, this user operation also causes the displaying of the findings information to be updated as illustrated in FIG. 11. In the example of FIG. 11, the findings information 334b updated to findings information 334e. In the findings information 334e, a character string 1102 for identifying the associated ROI information is inserted to a part 1101. In the example of FIG. 11, "6:" as the character string 1102 corresponding to ROI number 6 is inserted.

Figure 12A:
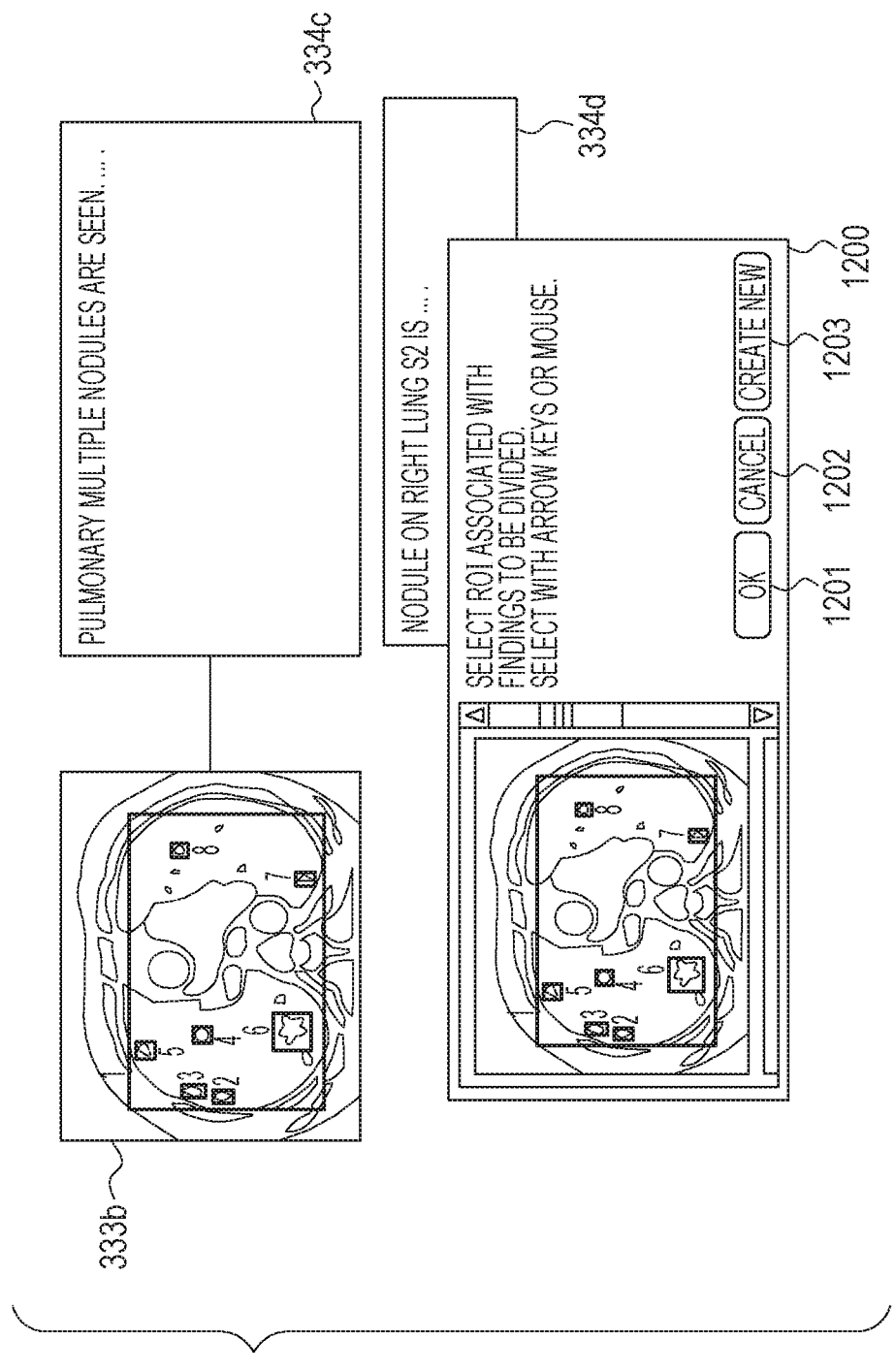
FIGS. 12A and 12B illustrate examples of region of interest (ROI) selection screens.

FIG. 12A illustrates an example of a ROI selection screen 1200 for selecting ROI information associated with findings information that is a divide target. On the ROI selection screen 1200, the medical display image 333b associated with the findings information 334c is displayed. The user can select a ROI in the medical display image 333b by using an arrow key or arrow keys or clicking the mouse. Upon clicking an "OK" button 1201, the terminal apparatus 100 determines that the selected ROI is the ROI to be associated with the findings information that is a divide target. Upon clicking a "cancel" button 1202, the terminal apparatus 100 terminates the selection process. Upon clicking a "create new" button 1203, the terminal apparatus 100 can create a new ROI on the viewer screen 310.

Figure 12B:
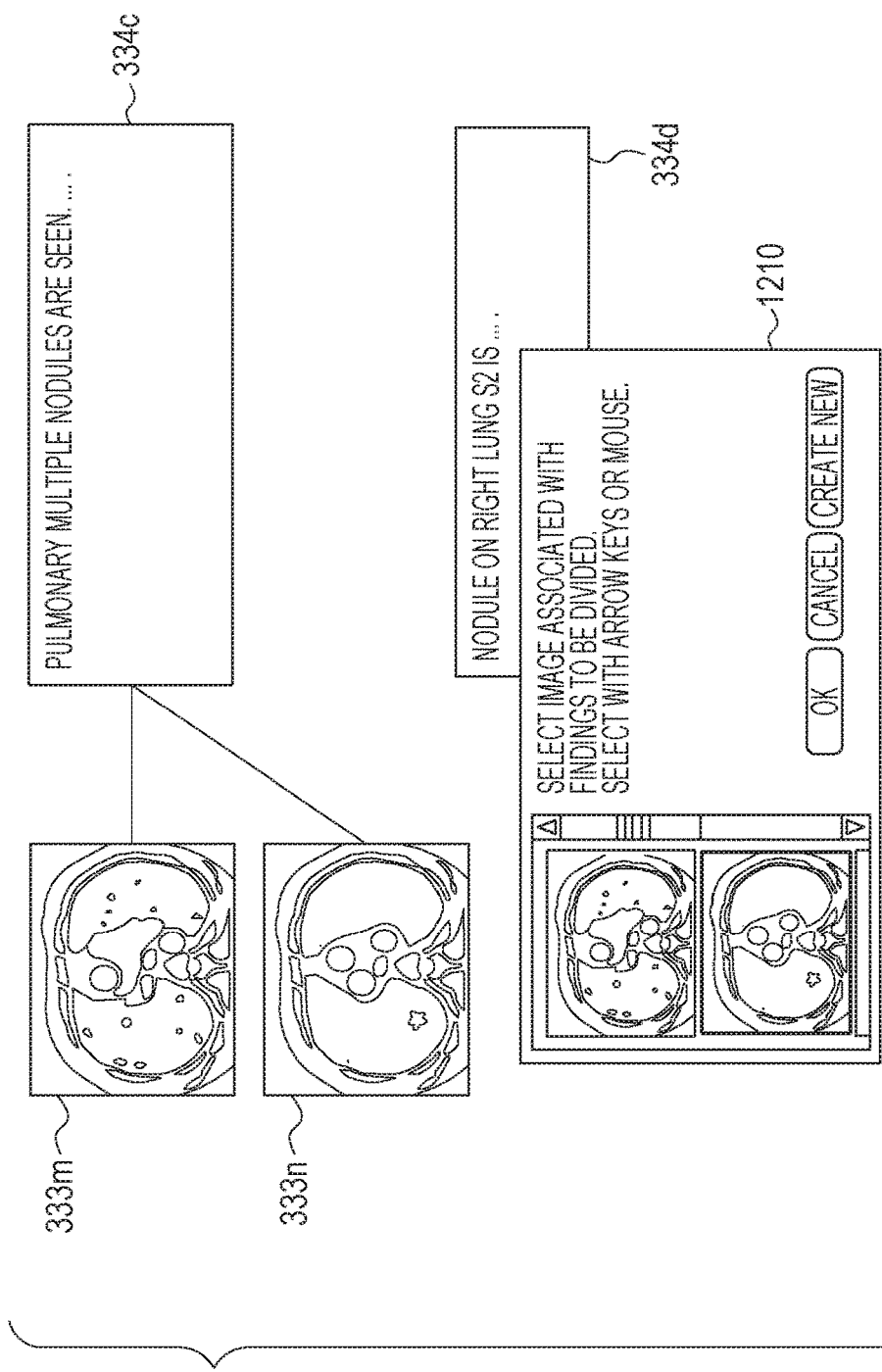
Figure 13A:
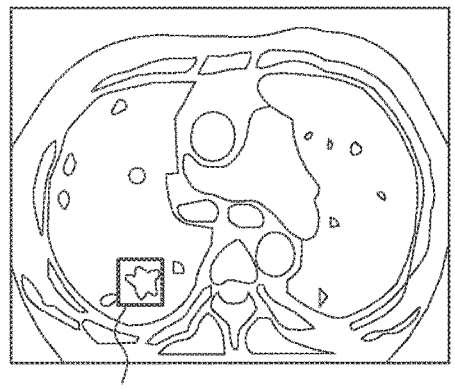
FIGS. 13A, 13B, 13C, and 13D illustrate shapes of ROI icons.
Figure 13B:
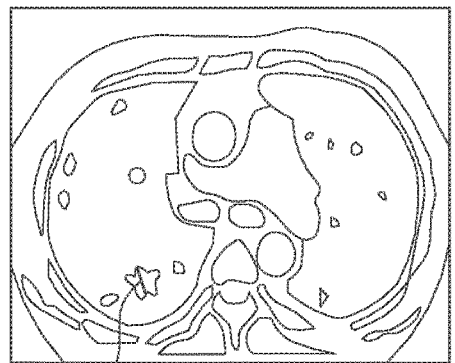
Figure 13C:
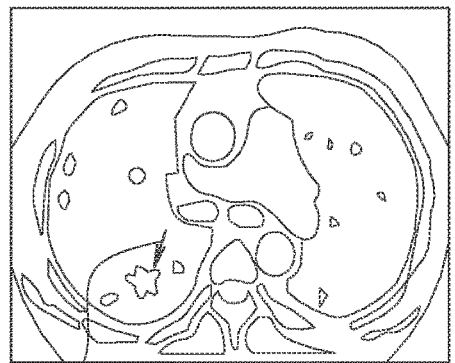
Figure 13D:
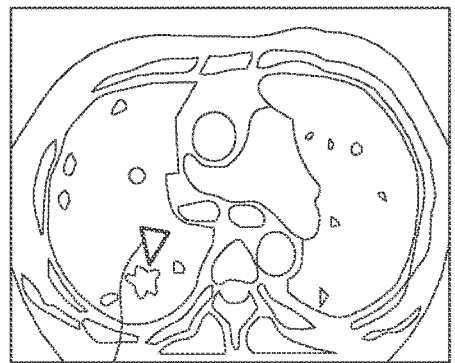

FIG. 12B illustrates an example of an image selection screen 1210 for selecting a representative image to be associated with findings information that is a divide target when generating the representative image. If two representative images 333m and 333n are associated with the findings information 334c that, is a divide target, the two representative images 333m and 333n are displayed on the image selection screen 1210. Also in this case, the terminal apparatus 100 can select a ROI or create a new ROI in accordance with a user operation that is the same or substantially the same as the operation on the ROI selection screen. 1200.

FIGS. 13A, 13B, 13C, and 13D illustrate shapes of icons for specifying a ROI. The shapes of icons for specifying a ROI are a rectangle 1301 illustrated in FIG. 13A, a straight line 1302 illustrated in FIG. 13B, an arrow 1303 illustrated in FIG. 13C, a triangle 1304 illustrated in FIG. 13D, and the like. Note that the shapes of the icons for specifying a ROI are not limited to the examples in FIGS. 13A to 13D and may be a circle, an ellipse, a polygon, and any other shape.

Figure 14A:
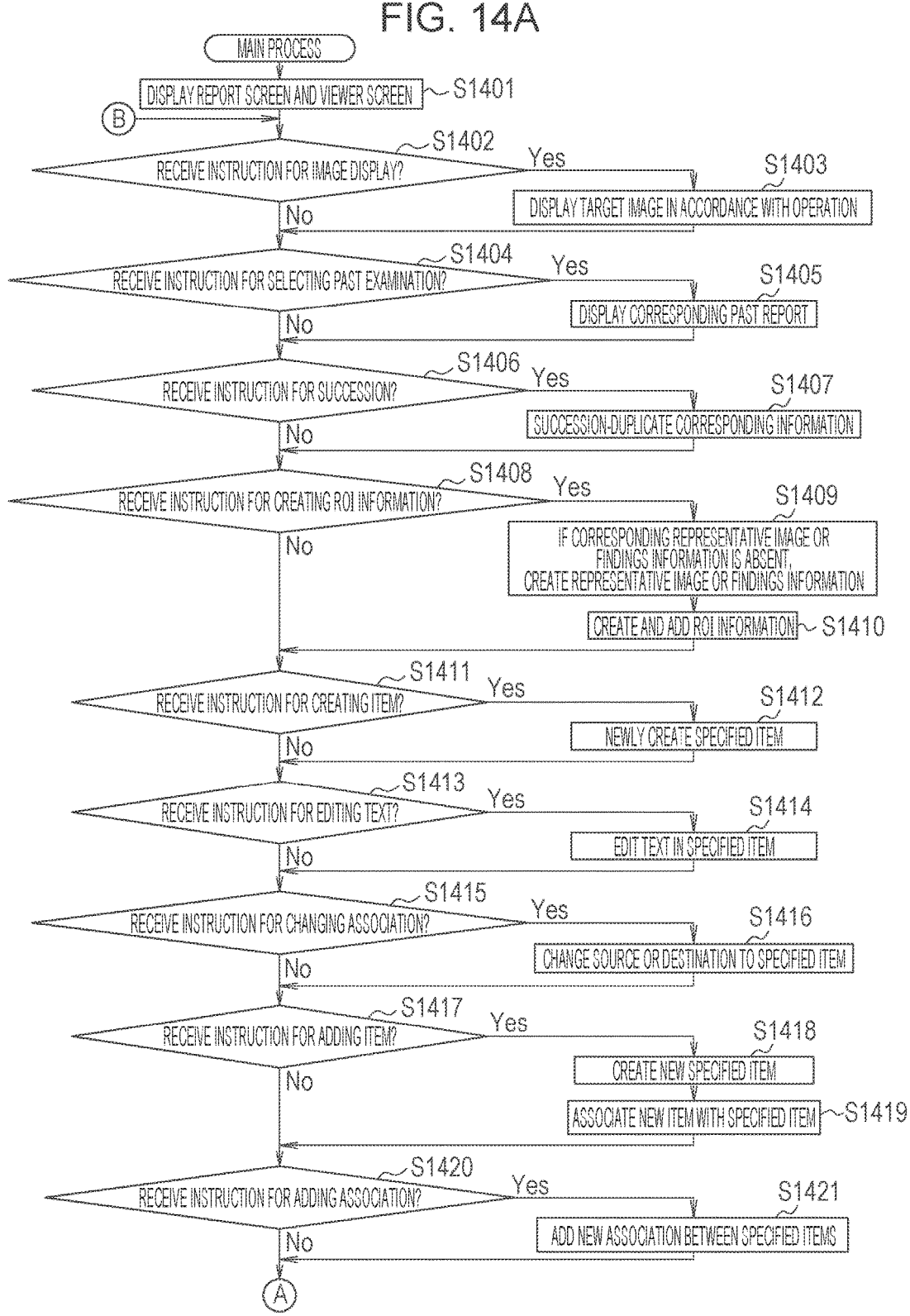
FIGS. 14A and 14B are a flowchart illustrating a main process.
Figure 14B:
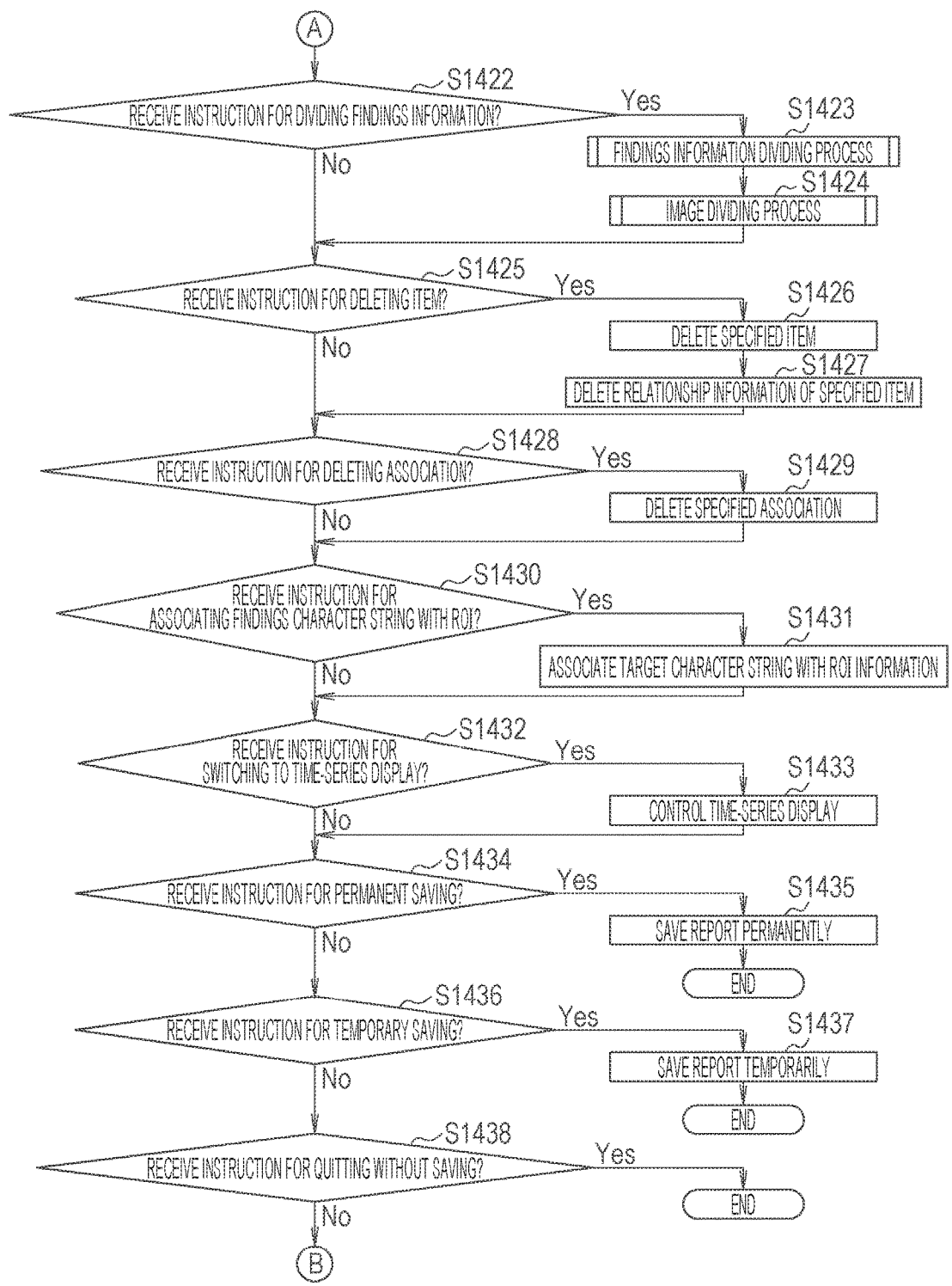

FIGS. 14A and 14B are a flowchart illustrating a main process performed by the terminal apparatus 100. In step S1401, the display processing unit 411 reads image information from the image DB 121. The display processing unit 411 further reads radiographic interpretation report information from the report DB 131. On the basis of the image information and the radiographic interpretation report information, the display processing unit 411 per control so as to display the viewer screen 310 and the report screen 320. Then, in step S1402, upon receiving, through the viewer screen 310, an instruction for image display for, for example, forwarding slice images or changing conditions for image display (YES in step S1402), the receiving unit 412 causes the process to proceed to step S1403. If an instruction for image display is not received (NO in step S1402), the CPU 202 causes the process to proceed to step S1404.

In step S1403, the display processing unit 411 changes the displaying of a target image in accordance with the display instruction. Then, in step S1404, upon receiving an instruction for selecting a past examination through the control 331 on the report screen 320 (YES in step S1404), the receiving unit 412 causes the process to proceed to step S1405. If an instruction for selecting a past examination is not received (NO in step S1404), the receiving unit 412 causes the process to proceed to step S1406.

In step S1405, the display processing unit 411 reads radiographic interpretation report information related to the selection instruction from the report DB 131 so as to display the radiographic interpretation report information on the report screen 320. Then, in step S1406, upon receiving a succession instruction for findings information (YES in step S1406), the receiving unit 412 causes the process to proceed to step S1407. If a succession instruction for findings information is not received (NO in step S1406), the receiving unit 412 causes the process to proceed to step S1408.

In step S1407, the editing unit 413 succession-duplicates information related to the succession instruction to current radiographic interpretation report information. The receiving unit 412 receives the succession instruction upon the user clicking the button 602 for succession. Succession-duplicated information is information having a chronological relationship with past findings. The information from which the succession-duplicated information is generated is selected by a user operation, and the selected information is highlighted. In accordance with a user operation, the editing unit 413 creates a report or performs other editing operations on the information selected by the user operation unless otherwise specified below.

Then, in step S1408, upon receiving an instruction for creating ROI information (YES in step S1408), the receiving unit 412 causes the process to proceed to step S1409. If an instruction for creating ROI information is not received (NO in step S1408), the receiving unit 412 causes the process to proceed to step S1411. In step S1409, if there is no representative image corresponding to the image for which the ROI was created, the editing unit 413 creates a representative image, and if there is no findings information corresponding to a representative image, the editing unit 413 creates findings information. Then, in step S1410, the editing unit 413 creates the ROI information and associates the ROI information with the corresponding representative image. The association here is processing for recording the ROI information, the findings information, and the representative image in association with one another and is, in this embodiment, processing for adding the ROI information, the findings information, and the representative image to the same radiographic interpretation report information.

Then, in step S1411, upon receiving an instruction for creating an item (YES in step S1411), the receiving unit 412 causes the process to proceed to step S1412. The item here corresponds to an information type such as findings, diagnosis, or recommendation. If an instruction for creating an item is not received (NO in step S1411), the receiving unit 412 causes the process to proceed to step S1413. In step 1412, the editing unit 413 newly creates the item related to the creation instruction.

Then, in step S1413, upon receiving an instruction for editing text in the item (YES in step S1413), the receiving unit 412 causes the process to proceed to step S1414 if an instruction for editing text is not received (NO in step S1413), the receiving unit 412 causes the process to proceed to step S1415. In step S1414, the editing unit 413 edits text in the specified item in accordance with the edit instruction. Editing text here means inputting characters, deleting characters, selecting a character string, cutting a character string, copying a character string, pasting a character string, and the like.

Then, in step S1415, upon receiving an instruction for changing association (YES in step S1415), the receiving unit 412 causes the process to proceed to step S1416. If an instruction for changing association is not received (NO in step S1415), the receiving unit 412 causes the process to proceed to step S1417. In step S1416, the editing unit 413 changes a source or destination to the specified item in accordance with the change instruction. Note that if the user drag-and-drops an end of a line indicating the association, the receiving unit 412 receives a change instruction that specifies the dropped item as the new source or destination.

In step S1417, upon receiving an instruction for adding an item (YES in step S1417), the receiving unit 412 causes the process to proceed to step S1418. If an instruction for adding an item is not received (NO in step S1417), the receiving unit 412 causes the process to proceed to step S1420. In step S1418, the editing unit 413 creates a new item related to the adding instruction. Then, in step S1419, the editing unit 413 associates the new item related to the adding instruction with a specified item. For example, if the user specifies certain findings information and pushes a tab key, the editing unit 413 creates diagnosis information associated with the selected findings information. Similarly, if the user specifies certain diagnosis information and pushes a tab key, the editing unit 413 creates recommendation information associated with the diagnosis information. In addition, if the user specifies certain diagnosis information and pushes a predetermined shortcut key, the editing unit 413 adds new diagnosis information to findings information associated with the diagnosis information. The operation for adding the item is not limited to the above exemplary operation.

Then, in step S1420, upon receiving an instruction for adding association (YES in step S1420), the receiving unit 412 causes the process to proceed to step S1421. If an instruction for adding association is not received (NO in step S1420), the receiving unit 412 causes the process to proceed to step S1422. In step S1421, the editing unit 413 performs processing for associating a plurality of specified items related to the adding instruction. For example, if the user drag-and-drops certain findings information on certain diagnosis information, the receiving unit 412 receives an adding instruction, and the editing unit 413 associates the findings information with the diagnosis information related to the drag-and-drop operation. Note that the user operation corresponding to the instruction for adding association is not limited to the above exemplary operation.

Then, in step S1422, upon receiving an instruction for dividing findings information (YES in step S1422), the receiving unit 412 causes the process to proceed to step S1423. If an instruction for dividing findings information is not received (NO in step S1422), the receiving unit 412 causes the process to proceed to step S1425. Here, step S1422 is exemplary processing for receiving a divide instruction. In step S1423, the editing unit 413 performs a findings information dividing process. Then, in step S1424, the editing unit 413 performs an image dividing process. Note that the findings information dividing process (51423) and the image dividing process (S1424) will be described later in detail with reference to FIGS. 15 and 16, respectively.

Note that an example of a user operation for inputting the divide instruction may be an operation for associating a character string in findings information with certain diagnosis information as illustrated in FIG. 7A. Other examples are an operation for adding a new diagnosis by specifying a character string and pushing a tab key, an operation for pushing a shortcut key, an operation for selecting a menu, and the like.

Then, in step S1425, upon the receiving an instruction for deleting an item (YES in step S1425), the receiving unit 412 causes the process to proceed to step S1426. If an instruction for deleting an item is not received (NO in step S1425), the receiving unit 412 causes the process to proceed to step S1428. In step S1426, the editing unit 413 deletes the item related to the deleting instruction. Then, in step S1427, the editing unit 413 also deletes relationship information related to the item according to the deleting instruction. Note that if the user pushes a "Delete" key with an item specified by using the mouse or an arrow key or arrow keys, the receiving unit 412 receives an instruction for deleting the item.

Then, in step S1428, upon receiving an instruction for deleting association (YES in step S1428), the receiving unit 412 causes the process to proceed to step S1429. If an instruction for deleting association is not received (NO in step S1428), the receiving unit 412 causes the process to proceed to step S1430. In step S1429, the editing unit 413 deletes association related to the deleting instruction. Note that if the user clicks a line indicating association with the mouse and pushes the "Delete" key with the line selected, the receiving unit 412 receives an instruction for deleting the association.

Then, in step S1430, upon receiving an instruction for associating a character string in findings information with a ROI (YES in step S1430), the receiving unit 412 causes the process to proceed to step S1431. If an association instruction is not received (NO in step S1430), the receiving unit 412 causes the process to proceed to step S1432. In step S1431, the receiving unit 412 associates the target character string with ROI information. Note that if the user selects a character string in findings information and drag-and-drops the character string on certain ROI information as illustrated in FIG. 11, the receiving unit 412 receives an association instruction.

In addition, associating the character string in findings information with the ROI information is processing for inserting the ROI information (character string for identifying ROI) into the character string at (in front of or behind) a predetermined position. As another example, the above associating may be processing for generating relationship information of the findings information and the ROI information and adding the relationship information to the radiographic interpretation report information 500.

Then, in step S1432, upon receiving an instruction for switching to time-series display (YES in step S1432), the receiving unit 412 causes the process to proceed to step S1433. If an instruction for switching to time-series display is not, received (NO in step S1432), the receiving unit 412 causes the process to proceed to step S1434. In step S1433, the editing unit 413 controls the time-series display described above with reference to FIG. 10 to be performed or terminated in accordance with the switching instruction. Note that if the user clicks the button 350 (see FIGS. 3A and 3B) for time-series display, the receiving unit 412 receives an instruction for switching to time-series display. In addition, if the user clicks the button 1002 (see FIG. 10) for displaying a report, the receiving unit 412 receives an instruction for terminating time-series display.

Then, in step S1434, upon receiving an instruction for permanent saving (YES in step S1434), the receiving unit 412 causes the process to proceed to step S1435. If an instruction for permanent saving is not received (NO in step S1434), the receiving unit 412 causes the process to proceed to step S1436. Note that if the user performs an operation. such as clicking the button for permanent saving, the receiving unit 412 receives an instruction for permanent saving. In step S1435, the editing unit 413 causes the radiographic interpretation report information 500 to be stored permanently in the report DB 131.

Then, in step S1436, upon receiving an instruction for temporary saving (YES in step S1436), the receiving unit 412 causes the process to proceed to step S1437. If an instruction for temporary saving is not received (NO in step S1436), the receiving unit 412 causes the process to proceed to step S1438. Note that if the user performs an operation such as clicking the button for temporary saving, the receiving unit 412 receives an instruction for temporary saving. In step S1437, the editing unit 413 causes the radiographic interpretation report information to be stored temporarily. In step S1438, upon receiving an instruction for gutting without saving (YES in step S1438), the receiving unit 412 causes the process to end. If an instruction for quitting without saving is not received (NO in step S1438), the receiving unit 412 causes the process to proceed to step S1402. Note that if the user performs an operation such as clicking the button for quitting without saving, the receiving unit 412 receives an instruction for quitting without saving.

Figure 15:
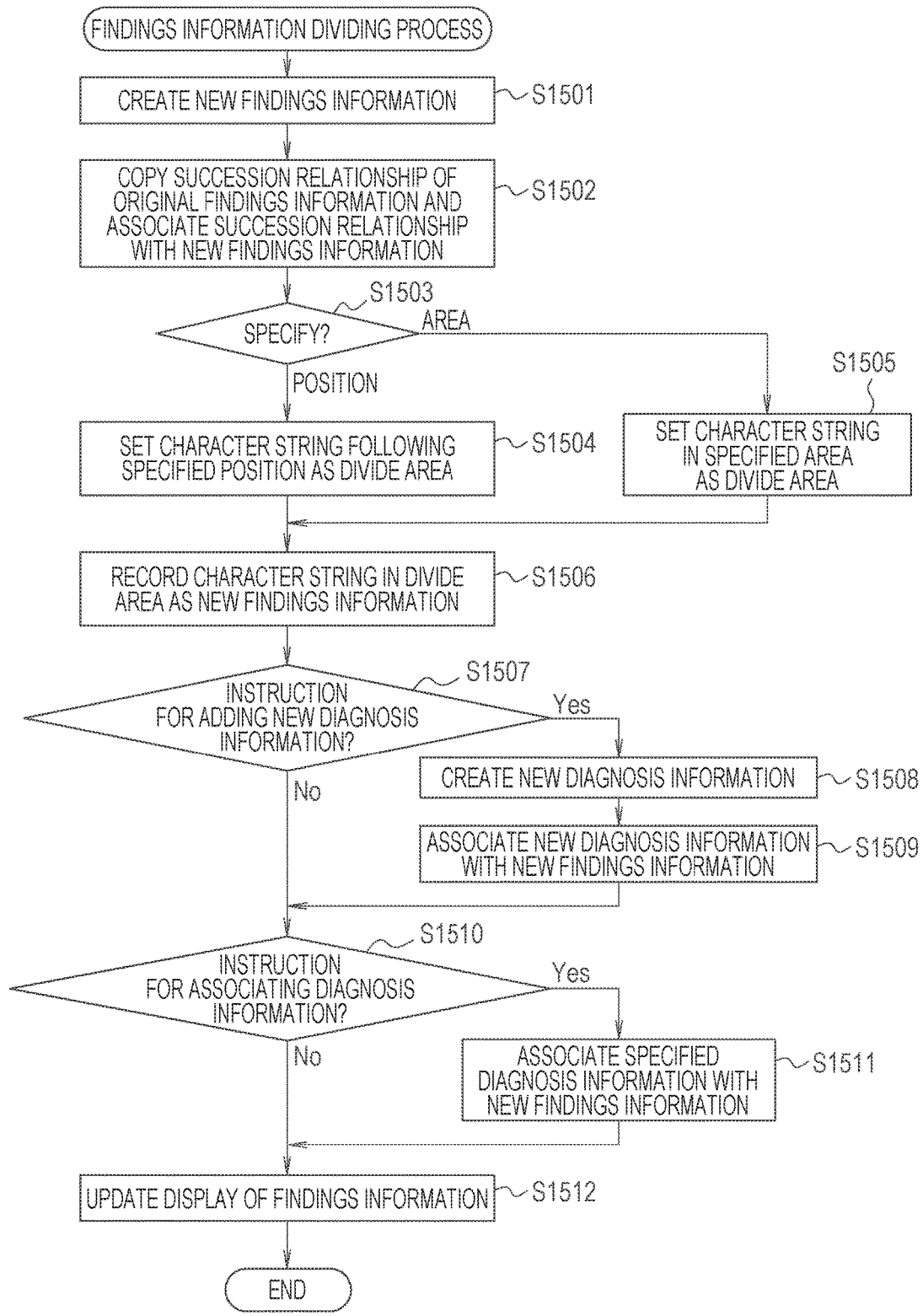
FIG. 15 is a flowchart illustrating a findings information dividing process.

FIG. 15 is flowchart illustrating details of the findings information dividing process (S1423) that has been described with reference to FIGS. 14A and 14B. In step S1501, the editing unit 413 creates new findings information and records the findings information in the radiographic interpretation report information 500. Then, in step S1502, the editing unit 413 copies a succession relationship of original findings information and associates the succession relationship with the newly created findings information. Here, the information having a succession relationship means relationship information with a relationship type "succession" and indicates the correspondence relationship over time between the past findings and the current findings described with reference to FIG. 5.

Then, in step S1503, the editing unit 413 checks the method for specifying a divide area in the divide instruction. If a divide position has been specified ("POSITION" in step S1503), the editing unit 413 causes the process to proceed to step S1504. If a divide area has been specified. ("AREA" in step S1503), the editing unit 413 causes the process to proceed to step S1505. In step S1504, the editing unit 413 sets the character string following the specified divide position as a divide area, and then the process proceeds to step S1506. In step S1505, the editing unit 413 sets the specified area as the divide area, and the process proceeds to step S1506.

In step S1506, the editing unit 413 records the character string in the divide area as the new findings information created in step S1501. That is, the editing unit 413 records the character string in the divide area as the findings information in the radiographic interpretation report information. In addition, the editing unit 413 deletes the character string in the divide area from the original findings information. Here, the operation for dividing the findings information with the divide position specified is a predetermined shortcut key operation with a mouse cursor within text of the findings information, and the character string behind the mouse cursor is the divide area. In addition, the operation for dividing the findings information with the divide position specified is a predetermined shortcut key operation with an area of text of the finding information specified, and the specified area of text is the divide area.

Then, in step S1507, upon receiving an instruction for adding new diagnosis information together with the divide instruction. (YES in step S1507), the receiving unit 412 causes the process to proceed to step S1508. If an instruction for adding new diagnosis information is not received (NO in step S1507), the editing unit 413 causes the process to proceed to step S1510. In step S1508, the editing unit 413 creates new diagnosis information. Then, in step S1509, the editing unit 413 associates the newly created diagnosis information with the new findings information created in step S1501.

Then, in step S1510, upon receiving an instruction for associating existing diagnosis information together with the divide instruction (YES in step S1510), the receiving unit 412 causes the process to proceed to step S1511. If an instruction for associating existing diagnosis information is not received (NO in step S1510), the editing unit 413 causes the process to proceed to step S1512. In step S1511, the editing unit 413 associates the specified diagnosis information with the new findings information created in step S1501.

Then, in step S1512, the display processing unit 411 updates the displaying of the findings information. Specifically, as illustrated in FIG. 7B, the display processing unit 411 displays the information 700a as the new findings information 334d that is different from the findings information 334b. The display processing unit 411 further displays the new findings information 334c obtained by deleting the information 700a from the findings information 334b. Then, the findings information dividing process ends.

Figure 16:
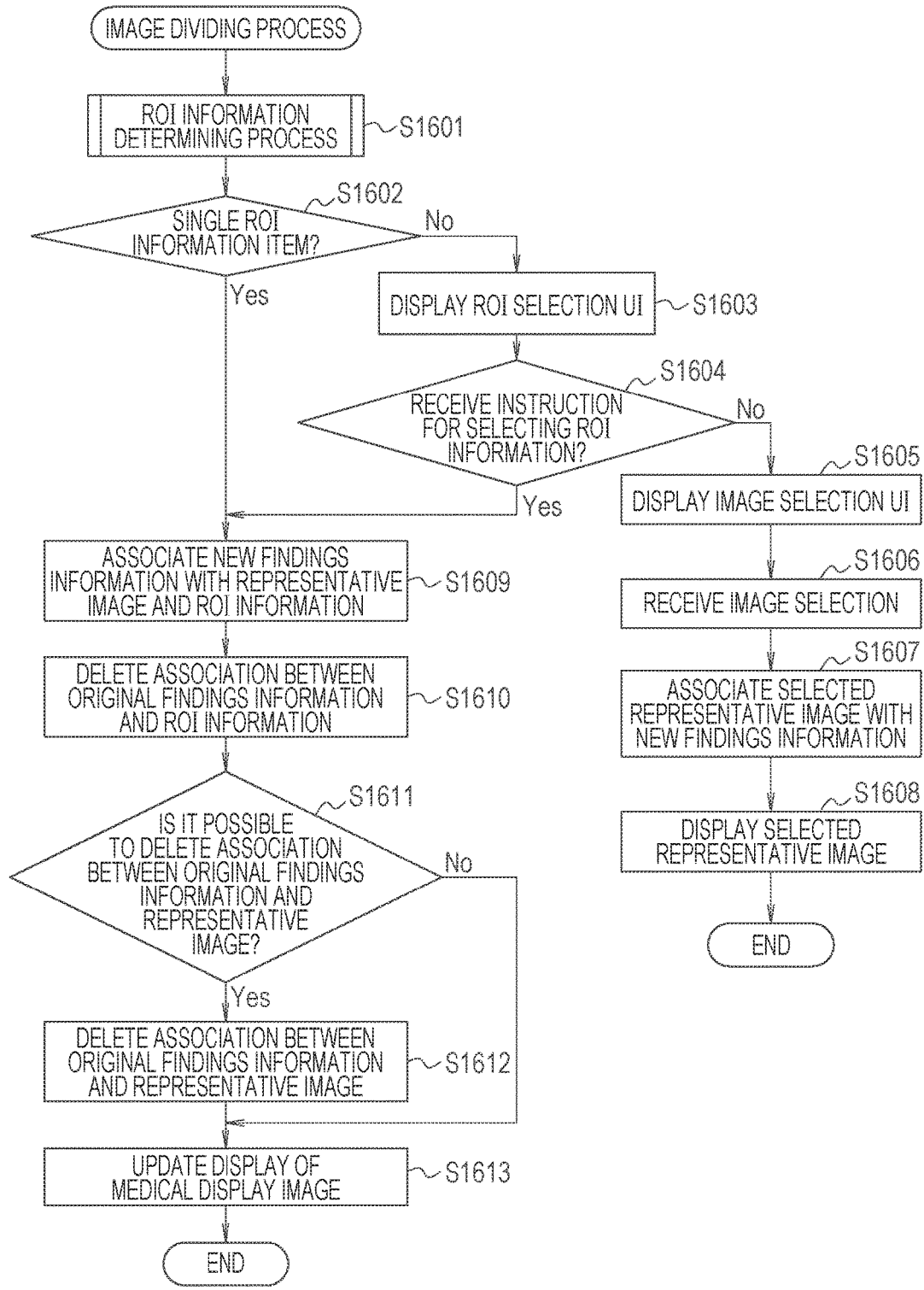
FIG. 16 is a flowchart illustrating an image dividing process.

FIG. 16 is a flowchart illustrating details of the image dividing process (S1424) that has been described with reference to FIGS. 14A and 14B, In step S1601, the editing unit 413 determines ROI information corresponding to findings information that has been generated in response to the divide instruction from among ROI information items associated with the original representative image. Note that the ROI information determining process will be described later in detail with reference to FIG. 17.

Then, in step S1602, if a single ROI information item has been determined (YES, in step S1602), the editing unit 413 causes the process to proceeds to step S1609. If a single ROI information has not been determined, that is, if a plurality of ROI information items have been determined, or there is no determined ROI information item (NO in step S1602), the editing unit 413 causes the process to proceed to step S1603. In step S1603, the display processing unit 411 displays the ROI selection screen 1200 (see FIG. 12A). Then, in step S1604, upon receiving an instruction for selecting a ROI in accordance with a user operation (YES in step S1604), the receiving unit 412 causes the process no proceed to step S1609. If a selection instruction is not received (NO in step S1604), the receiving unit 412 causes the process to proceed to step S1605.

In step S1605, the editing unit 413 displays the image selection screen 1210 (see FIG. 12B). Then, in step S1606, the receiving unit 412 receives user selection of a representative image. Then, in step S1607, the editing unit 413 records, in the radiographic interpretation report information, the selected representative image as a representative image corresponding to the new findings information created in step S1423. Specifically, the editing unit 413 records the new findings information and the representative image in association with each other. Then, in step S1608, the display processing unit 411 displays the selected representative image as a medical display image in association with the new findings information. Thus, processing for generating the representative image ends.

On the other hand, in step S1609, the editing unit 413 associates the new findings information with the ROI information determined in step S1601 or S1604, and the representative image associated with the ROI information. Then, in step S1610, the editing unit 413 deletes association between the original findings information and the ROI information determined in step S1601 or S1604.

Then, in step S1611, the editing unit 413 determines whether or not it is possible to delete association between the original findings information and the representative image that is associated with the original findings information and that is also associated with the new findings information. If the original findings information is not associated with the ROI information associated with the representative image, the editing unit 413 determines that it is possible to delete the association. If it is possible to delete the association (YES in step S1611), the editing unit 413 causes the process to proceed to step S1612. If it is not possible to delete the association (NO in step S1611), the editing unit 413 causes the process to proceed to step S1613. In step S1612, the editing unit 413 deletes the association between the original findings information and the representative image associated with the new findings information.

Then, in step S1613, the display processing unit 411 updates the displaying of the medical display image. Specifically, as illustrated in FIGS. 7B and 6, the display processing unit 411 displays the medical display image in association with the new findings information, the medical display image obtained by superimposing region images of ROI information corresponding to the details of the divide instruction. In addition, the display processing unit 411 updates the medical display in associated with the original findings information on the basis of the details of the divide instruction. Specifically, the display processing unit 411 deletes the region images of the ROI information corresponding to the details of toe divide instruction from the medial display image associated with the original findings information, thereby generating a new medical display image. Thus, the image dividing process ends.

Figure 17:
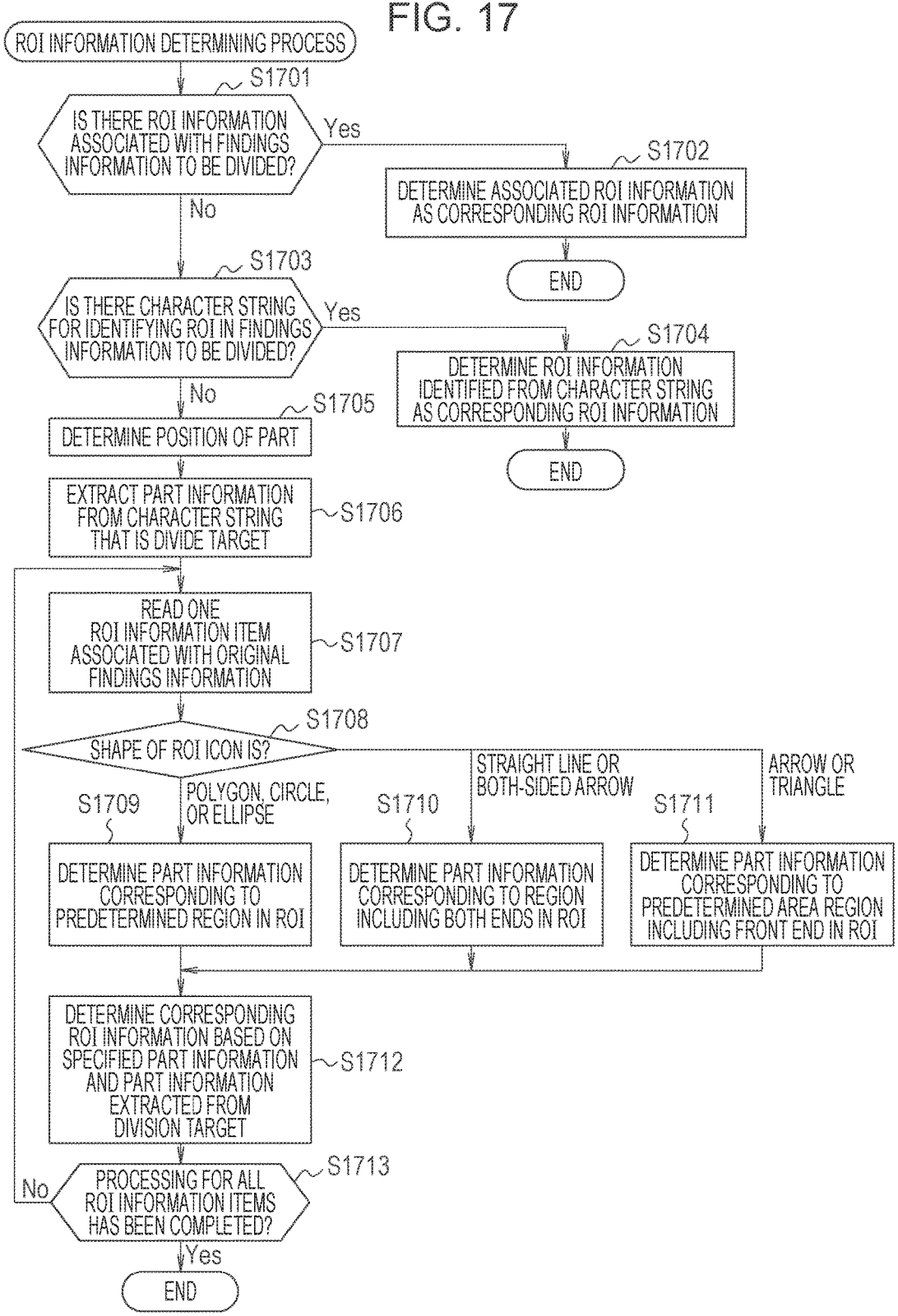
FIG. 17 is a flowchart illustrating a ROI information determining process.

FIG. 17 is a flowchart illustrating details of the ROI information determining process that has been described with reference to FIG. 16. In step S1701, on the basis of the radiographic interpretation report information 500, the editing unit 413 determines whether or not there is ROI information associated with a character string in the findings information to be divided. If there is ROI information (YES in step S1701), the process proceeds to step S1702. If there is no ROI information NO in step S1701), the editing unit 413 causes the process to proceed to step S1703. In step S1702, the editing unit 413 determines the associated ROI information as the ROI information corresponding to the new findings information that is generated in response to the divide instruction, and the process ends.

In step S1703, the editing unit 413 determines whether or not a character string for identifying ROI information is included in the findings information to be divided if a character string for identifying ROI information is included (YES in step S1703), the editing unit 413 causes the process to proceed to step S1704. If a character string for identifying ROI information is not included (NO in step S1703), the editing unit 413 causes the process to proceed to step S1705.

In step S1704, the editing unit 413 determines the ROI information identified from the character string as the ROI information corresponding to the new findings information, and the process ends. Here, the character string for identifying the ROI information is, for example, a character string including any of the above-described ROI numbers and a delimiter (e.g., "1:"). As another example, the character string for identifying the ROI information may be a character string expressing the shape or color of the ROI display frame (e.g., "white arrow", "yellow triangle", or "dashed-line square").

in step S1705, the editing unit 413 determines the position of a part of the image associated with the character string that is the divide target. Now, processing for determining the position of the part will be described. First, from DICOM information, the editing unit 413 obtains imaged part information, slice position information of the image, and information on the patient age and sex. Then, on the basis of the obtained information, the editing unit 413 obtains information on a corresponding human body model and a three-dimensional image. Here, the information on a human body model is information defining a standard position or area of an anatomy part, and the three-dimensional image is a series of slice images in the z-axis direction with a predetermined slice thickness.

Then, the editing unit 413 positions the three-dimensional image and the human body model. On the basis of the positioning result, the editing unit 413 determines the position and area of the part on the three-dimensional image. Here, the positioning means dividing the three-dimensional image into regions on the basis of changes in concentration, adjusting parameters for converting nonlinear coordinates, and minimizing the difference with the human body model. However, the positioning method is not limited to that in this embodiment. If there are a plurality of representative images associated with the original findings information and different three-dimensional images, the editing unit 413 performs the same or substantially the same processing on each of the three-dimensional images. Note that the method for determining the position of the part is not limited to that in this embodiment, and another determining method may be employed.

Then, in step S1706, the editing unit 413 extracts part information from the character string that is the divide target in the findings information. Through a morphological analysis on the character string and matching with a definition of the name of a part according to a dictionary, the part information is extracted. However, the method for extracting the part information is not limited to that in this embodiment. Then, in step S1707, the editing unit 413 determines the representative image associated with the original findings information and determines at least one ROI information items associated with the representative image. Then, the editing unit 413 reads one of the determined ROI information items.

Then, in step S1708, the editing unit 413 assesses the shape of a ROI icon. If the shape of the ROI icon is a rectangle, a polygon, a circle, or an ellipse ("POLYGON, CIRCLE, OR ELLIPSE" in step S1708), the editing unit 413 causes the process to proceed to step S1709. If the shape of the ROI icon is a straight line or both-sided arrow ("STRAIGHT LINE OR BOTH-SIDED ARROW" in step S1708), the editing unit 413 causes the process to proceed to step S1710. If the shape of the PCI icon is an arrow or a triangle ("ARROW OR TRIANGLE" in step S1708), the editing unit 413 causes the process to proceed to step S1711.

In step S1709, the editing unit 413 determines that the part corresponding to a predetermined region defined by the ROI icon is a ROI part and then causes the process to proceed to step S1712. In step S1710, the editing unit 413 determines that the part corresponding to a predetermined region including both ends of the ROI icon is the ROI part and then causes the process to proceed to step S1712. In step S1711, the editing unit 413 determines that the part corresponding to a predetermined region from the front end of the ROI icon toward the other end of the ROI icon is the ROI art and then causes the process to proceed to step S1712.

In step S1712, the editing unit 413 determines the ROI information in which the part indicated by the ROI information corresponds to the part information extracted from the character string that is the divide target. Then, the editing unit 413 determines the ROI information indicating the determined ROI as ROI information corresponding to the newly generated findings information. Then, in step S1713, the editing unit 413 determines whether or not processing in step S1707 through S1712 has been performed on all of the ROI information items corresponding to the original findings information. If the processing has been completed on all of the ROI information items (YES in step S1713), the editing unit 413 completes the ROI information determining process. If there is ROI information on which the processing has not been performed (NO in step S1713), the editing unit 413 causes the process to proceed to step S1707. Note that the findings information dividing process (S1423) and the image dividing process (S1414) are each an example of a registration process for registering new findings information (medical information), a corresponding target region, and a captured image as a representative image in a memory unit in association with one another.

As described above, if the findings information is divided, in response, the terminal apparatus 100 according to this embodiment can automatically update the association between the representative image and the findings information and the displaying of the association. Accordingly, it is possible to omit a user operation for registering association between a plurality of medical information items. In addition, even if the association between the character string that is the divide target in findings information and ROI information is not explicitly illustrated, the terminal apparatus 100 can automatically determine the corresponding ROI information and can generate the representative image. In addition, the terminal apparatus 100 can associate a selected character string with diagnosis information or, in accordance with addition of new generated diagnosis information, can associate the diagnosis information with findings information. In the above manner, the user operation can be omitted. Even if the group of lesions is changed, as described above, the terminal apparatus 100 can display medical information such that changes in lesions can be followed over time.

Now, modifications of a medical information display system according to this embodiment will be described. In this embodiment, if one findings information item is divided into plurality of findings information items, the terminal apparatus 100 records association between each division findings information and a corresponding ROI information item. Then, by depicting region images corresponding to the ROI information superimposed on a representative image during image display, the display processing unit 411 displays a medical display image. However, the terminal apparatus 100 may store information for displaying the medical display image and the findings information in association with each other in any data structure that is not limited to the data structure in this embodiment. As another example, if a divide instruction is received, the editing unit 413 may generate a medical display image to be displayed in association with findings information after dividing findings information and may record the generated medical display image and the findings information in association with each other. In this case, the display processing unit 411 may read and display the medical display image stored in association with the findings information when displaying the medical display image. That is, if a representative image is duplicated, the duplicated representative image is associated with new findings information, and there is no ROI information associated with the original representative image, the editing unit 413 may delete the original representative image.

Second Embodiment

Next, a medical information display system according to second embodiment will be described. In the medical information display system according to the second embodiment, the terminal apparatus 100 detects findings through CADe and combines medical documents in addition to dividing a medical document. Now, differences of the medical information display system according to the second embodiment from the medical information display system according to the first embodiment will be described below.

FIG. 18 illustrates an example of radiographic interpretation report information according to the second embodiment. Radiographic interpretation report information 1800 includes a plurality of medical information items and a plurality of relationship information items as in the radiographic interpretation report information 500. The radiographic interpretation report information 1800 includes medical information with an information type of "group findings". Hereinafter, medical information with an information type of "group findings" is referred to as "group findings information", as necessary. The group findings information includes attribute information such as UID, free text, name of part, lesion type, and a plurality of child information UIDs. Here, the child information UIDs are UIDs of findings information items to be included in a group.

Figure 19A:

FIG. 19A illustrates an example of the report screen 320 displayed when current radiographic interpretation report information is newly created. Findings information 334*f* indicates findings obtained by combining detection results through CADe. In the findings information 334*f*, "6: PART, RIGHT LUNG S2, FINDINGS, NODULE" and "7: PART, LEFT LUNG S1+S2, FINDINGS, NODULE" are each findings information detected through CADe. The findings information 334*f* includes such information items that are combined (as a group) and further includes the following information added by being input by a user such as a radiographic interpretation physician: "1: PULMONARY MULTIPLE NODULES ARE SEEN. NODULE ON RIGHT LUNG S2 IS . . . .". The other information on the report screen 320 is the same as that on the report screen 320 described in the first embodiment with reference to FIG. 6A.

Figure 19B:
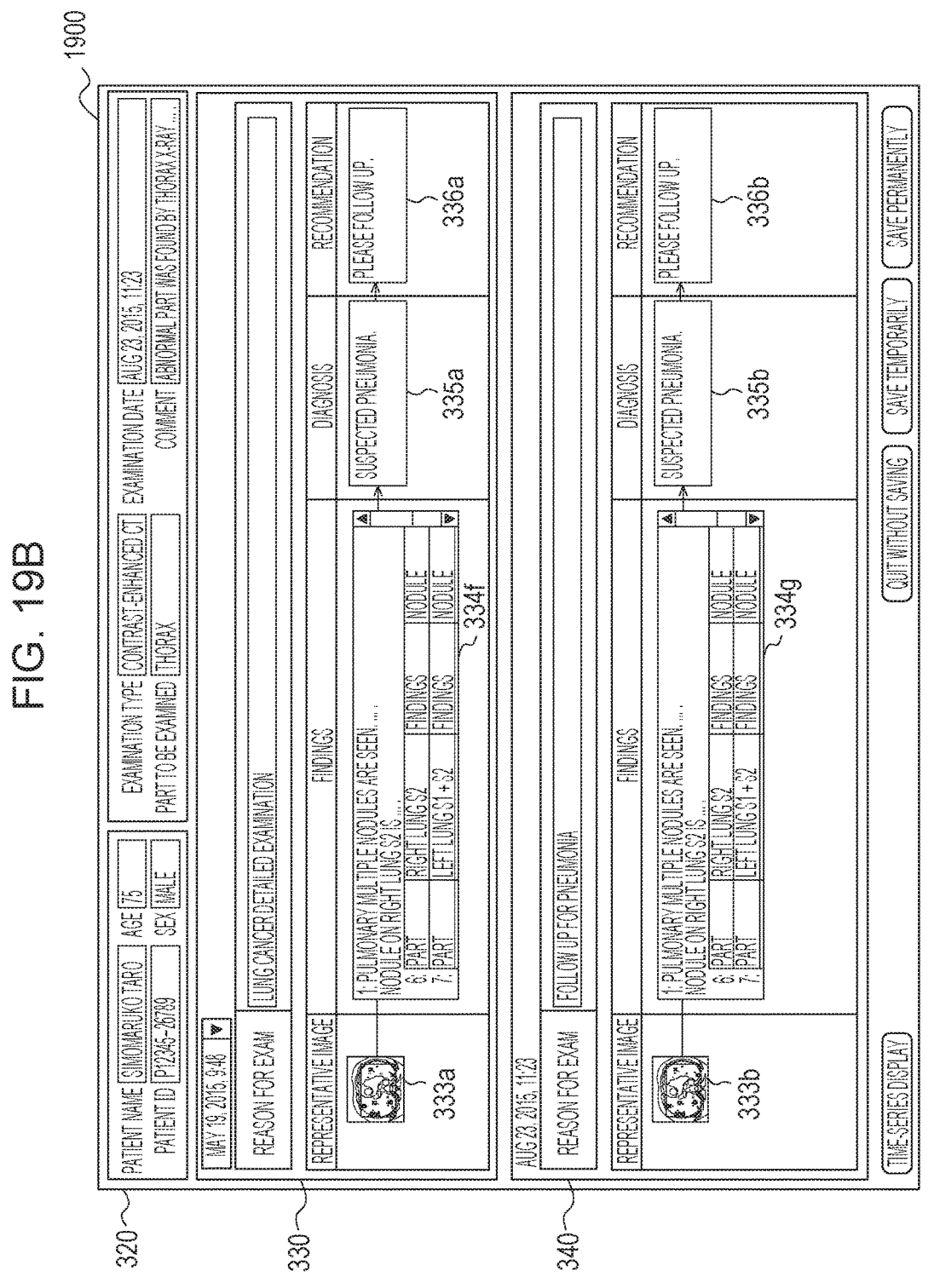

FIG. 19B illustrates an example of the, report screen 320 displayed after succession-duplicating. Findings information 334*g* indicates findings obtained by succession-duplicating the findings information 334*f*, and the findings information 334*g* and the findings information 334*f* have a succession relationship Note that the other information on the report screen 320 displayed after succession-duplicating is the same or substantially the same as that on the report screen 320 described in the first embodiment with reference to FIG. 6B.

Figure 20A:
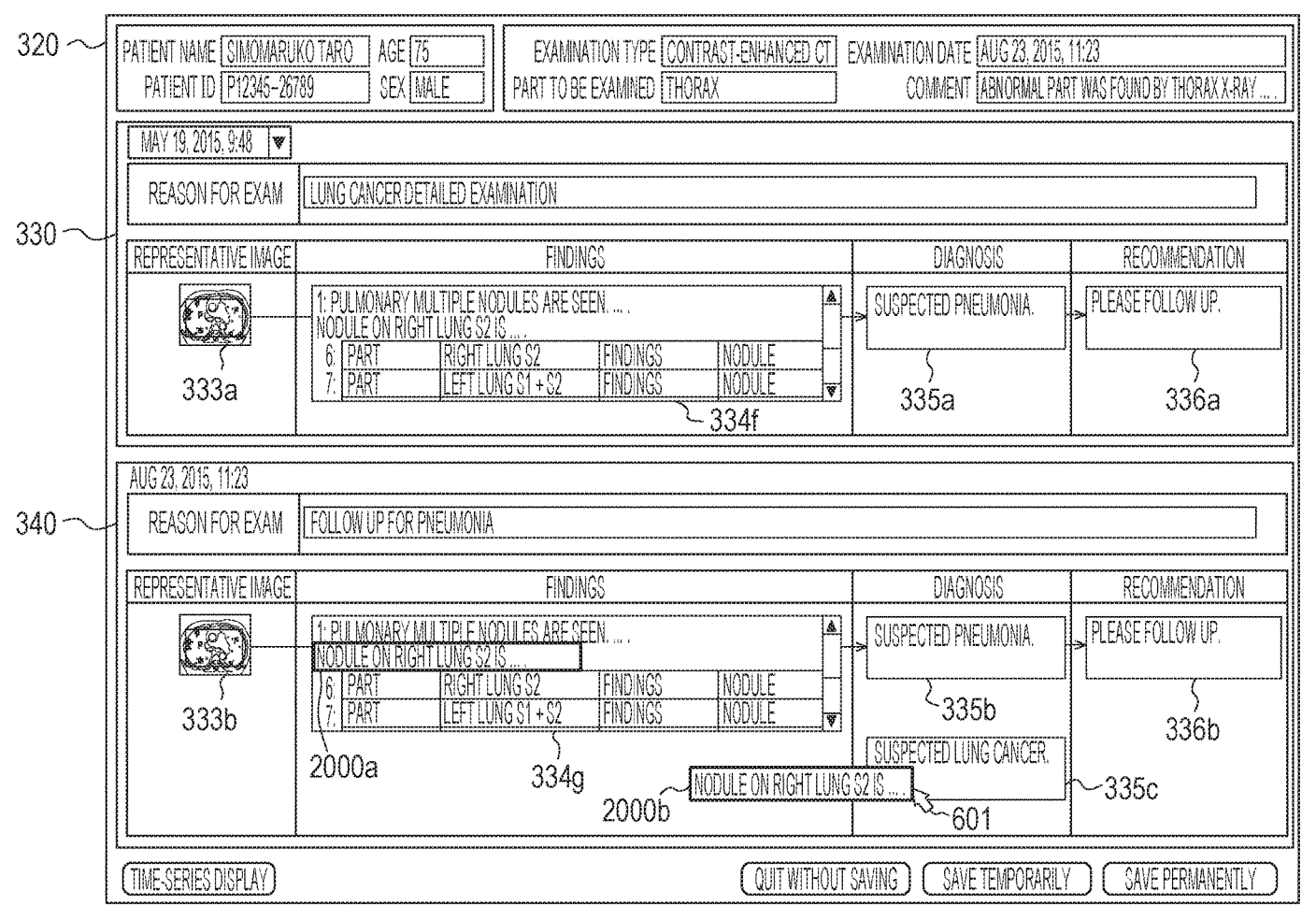
Figure 20B:
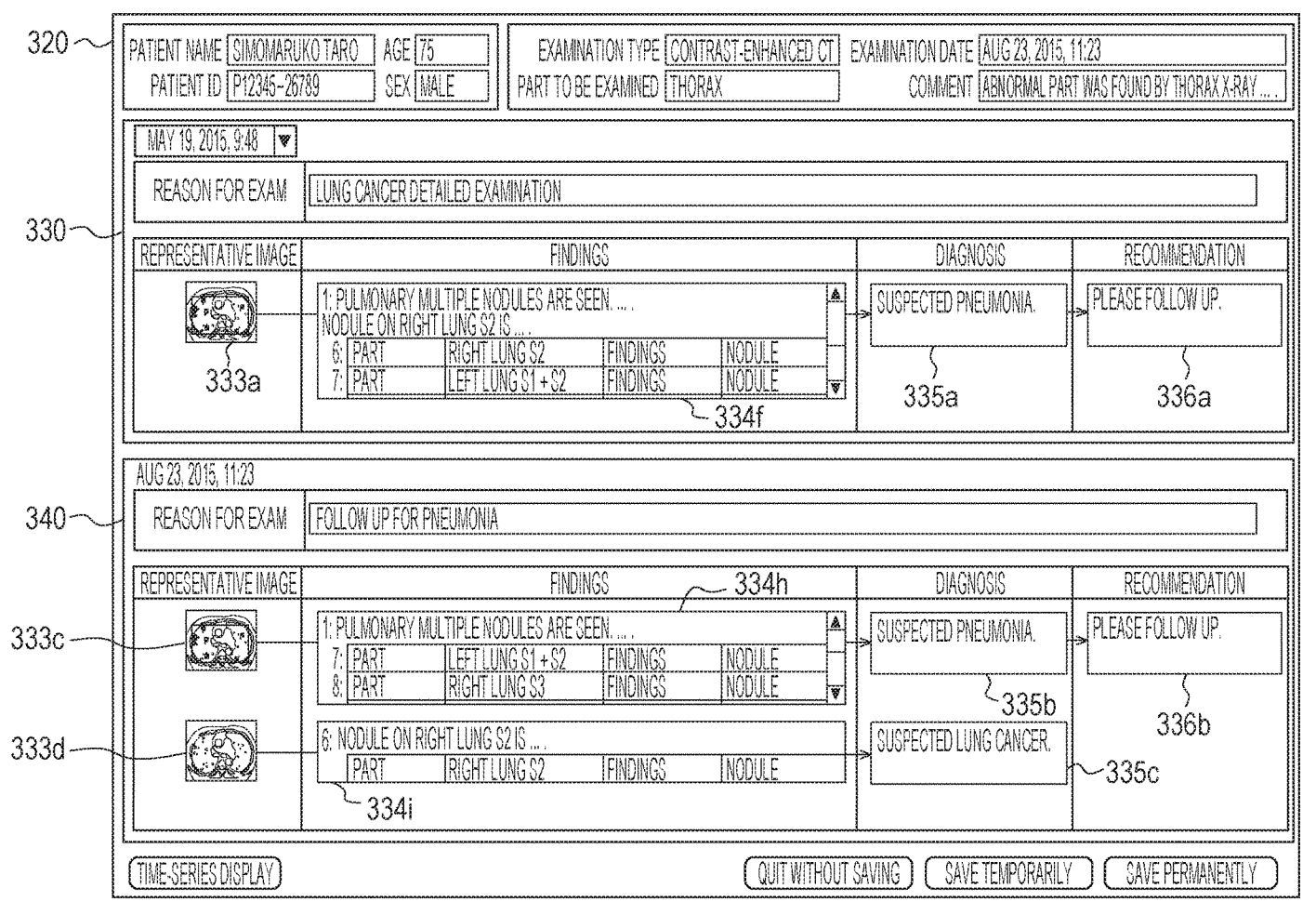

FIGS. 20A and 20B each illustrate an example of the report screen 320 when findings information is divided. FIG. 20A illustrates an example of the report screen 320 when an instruction for dividing findings information is input. If a user selects an area of a character string 2000*a*, "NODULE ON RIGHT LUNG S2 IS . . . ." in the findings information 334*g* and drag-and-drops the selected area on diagnosis information 335*c*. (2000*b*), the receiving unit 412 receives the divide instruction for dividing the findings information 334*g* to extract the character string 2000*a*. Upon receiving the divide instruction, the display processing unit 411 displays the character string 2000*a* as new findings information and deletes the character string 2000*a* from the findings information 334*g*.

FIG. 20B illustrates the report screen 320 after processing in response to the divide instruction. On the report screen 320 illustrated in FIG. 20B, in accordance with the divide instruction, the findings information 334*g* is divided into findings information 334*h* and findings information 334*i*. The findings information. 334*i* is a character string, "PART, RIGHT LUNG S2, FINDINGS, NODULE", which is a CADe result corresponding to a ROI. Note that the character string 2000*a* and "PART, RIGHT LUNG S2, FINDINGS, NODULE" are deleted in the findings information 334*h*.

Note that CADe detection results such as "6: PART, RIGHT LUNG S2, FINDINGS, NODULE" and "7: PART, LEFT LUNG S1+S2, FINDINGS, NODULE" can also be set as divide targets in findings information by selecting the corresponding row in the table and performing a drag-and-drop operation. The other display details are the same or substantially the same as the display details described in the first embodiment with reference to FIGS. 7A and 7B.

FIG. 21 illustrates a medical display image before and after dividing findings information. As described in the first embodiment with reference to FIG. 8, when the findings information 334*g* is divided into the findings information 334*h* and the findings information 334*i*, on the basis of the correspondence relationship between a dividing-related character string and ROIs, the medical display image 333*c*. and the medical display image 333*d* are generated and displayed.

FIG. 22 illustrates processing for combining findings information and medical display images. It is assumed that findings information 334*i* obtained by combining a plurality of findings information items with findings information 334*k* to generate the findings information 334*g*. Note that a medical display image 333*l* and a medical display image 333*k* are displayed in association with the findings information 334*j* and findings information 334*k*, respectively. In this case, in accordance with combining the findings information items, the medical display image 333*b* corresponding to the findings information 334*g* is generated and displayed. On the medical display image 333*b* displayed here, region images on the medical display image 333*j* and the medical display image 333*k* are superimposed. Note that the combining process will be described later with reference to FIGS. 27 and 28.

Figure 23:
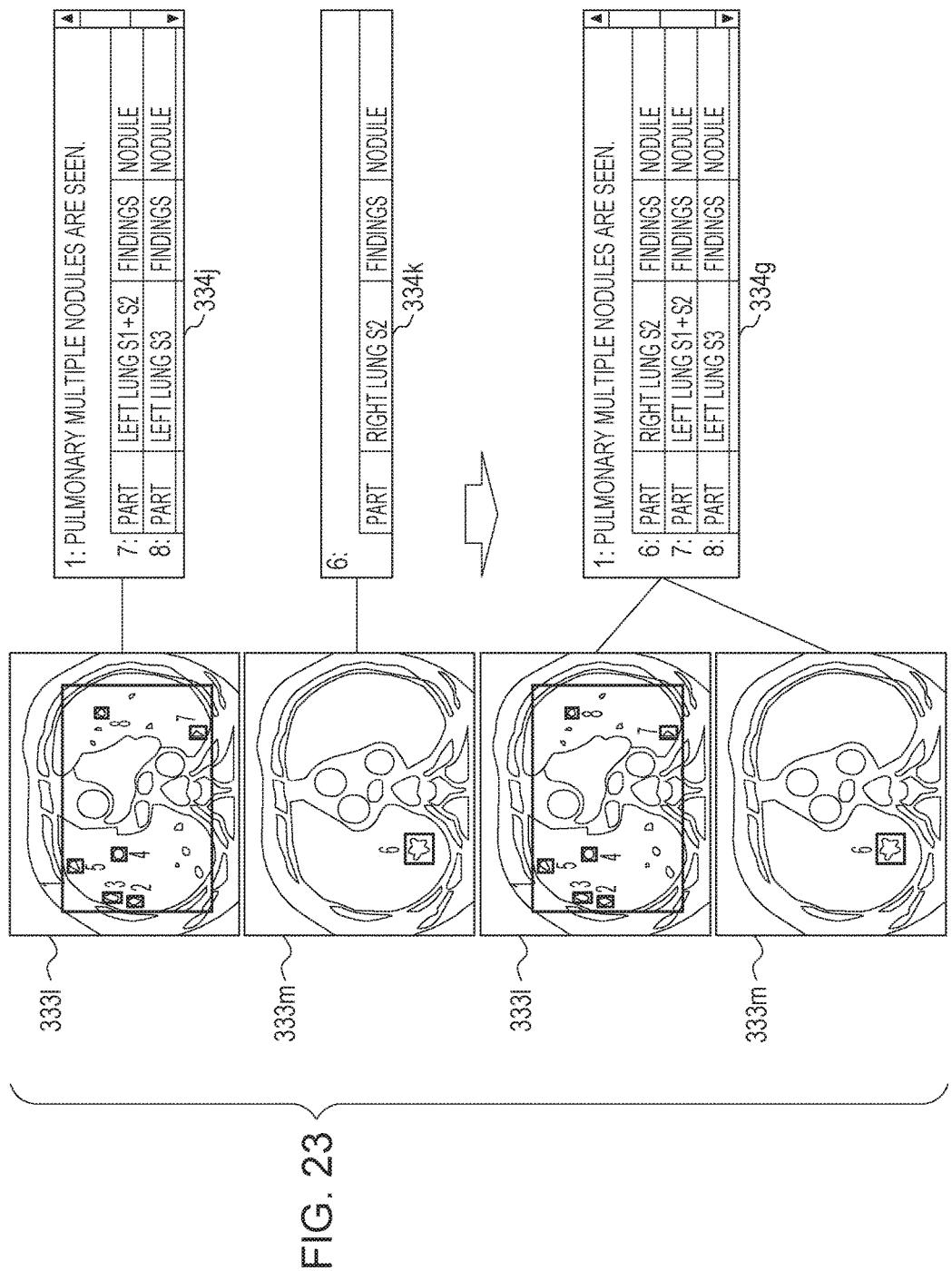
FIG. 23 illustrates an example of findings information and the like that are displayed.

FIG. 23 illustrates an example of findings information and the like displayed when medical display images are not combined at the time of combining findings information items. Slice positions for a medical display image 333*l* and a medical display image 333*m* are different. The medical display images corresponding to representative images at different slice positions are not combined at the time of combining the corresponding findings information 334*j* and findings information 334*k*. That is, as illustrated. in FIG. 23, each of the medical display images 333*l* and 333*m* is displayed in association with the findings information 334*g*.

Figure 24:
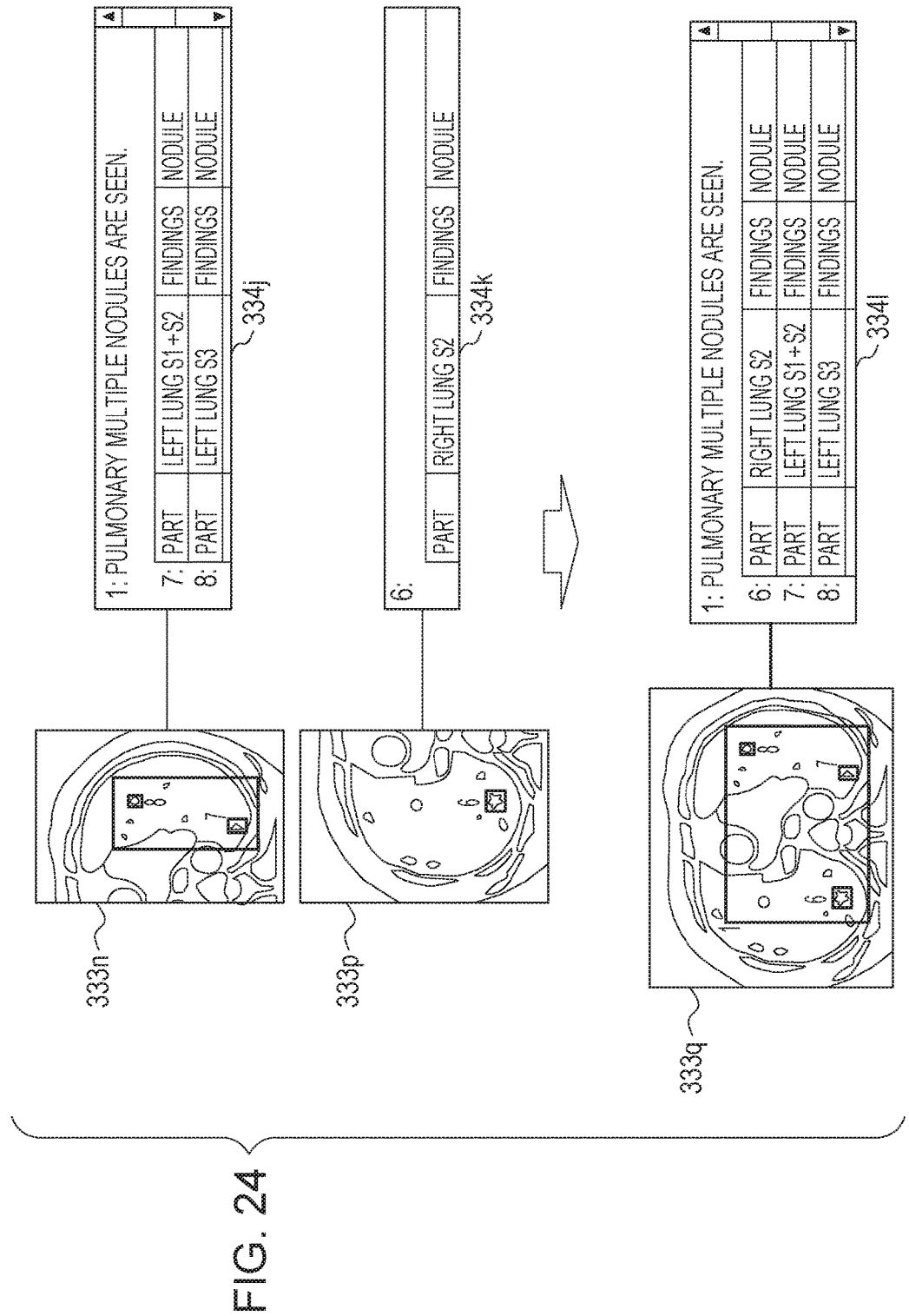
FIG. 24 illustrates examples of representative images and the like that are displayed.

FIG. 24 illustrates examples of medical display images and the like displayed when medical display images with different fields of view (FOV) are combined. Here, the FOV means a display area on a slice image. A medical display image 333*n*. and a medical display image 333*p* are the same slice image but have different FOVs. Accordingly, in this case, the terminal apparatus 100 generates a medical display image 333*q* as a combined image with an FOV including both of the above FOVs. Note that a ROI (with ROI number 1) corresponding to the combined findings information items (group of findings information items) is automatically changed to an area including a ROI (with ROI number 6) corresponding to the findings information to be combined.

Figure 25:
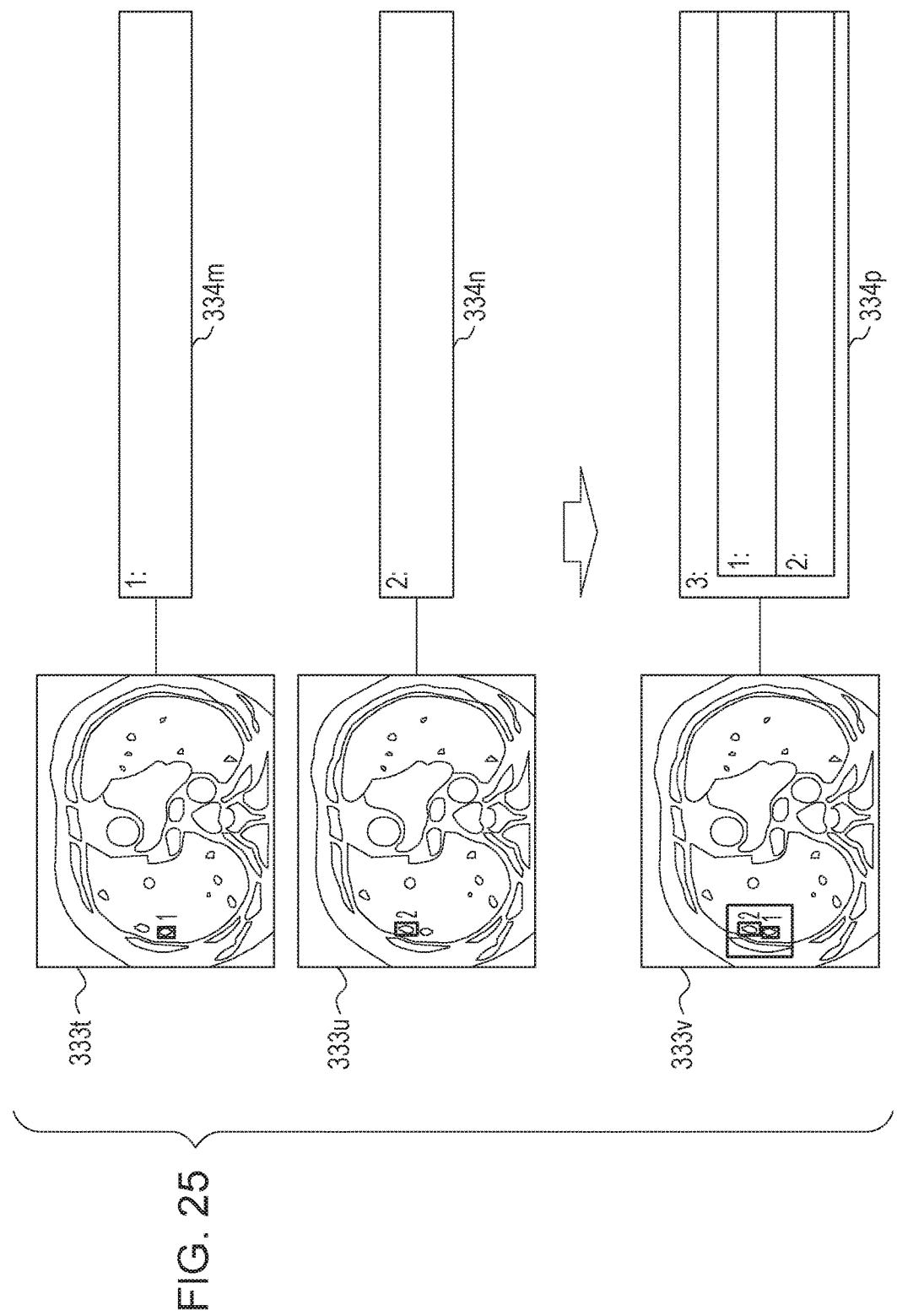
FIG. 25 illustrates a group of findings information.

As another example, as illustrated in FIG. 25, if findings information 334*m* and findings information 334*n* are combined, the terminal apparatus 100 may generate findings information (group of findings information items) corresponding to a ROI with ROI number 3. In addition, the terminal apparatus 100 may present input frames of findings information corresponding to ROIs with ROI numbers 1 and 2.

Figure 26A:
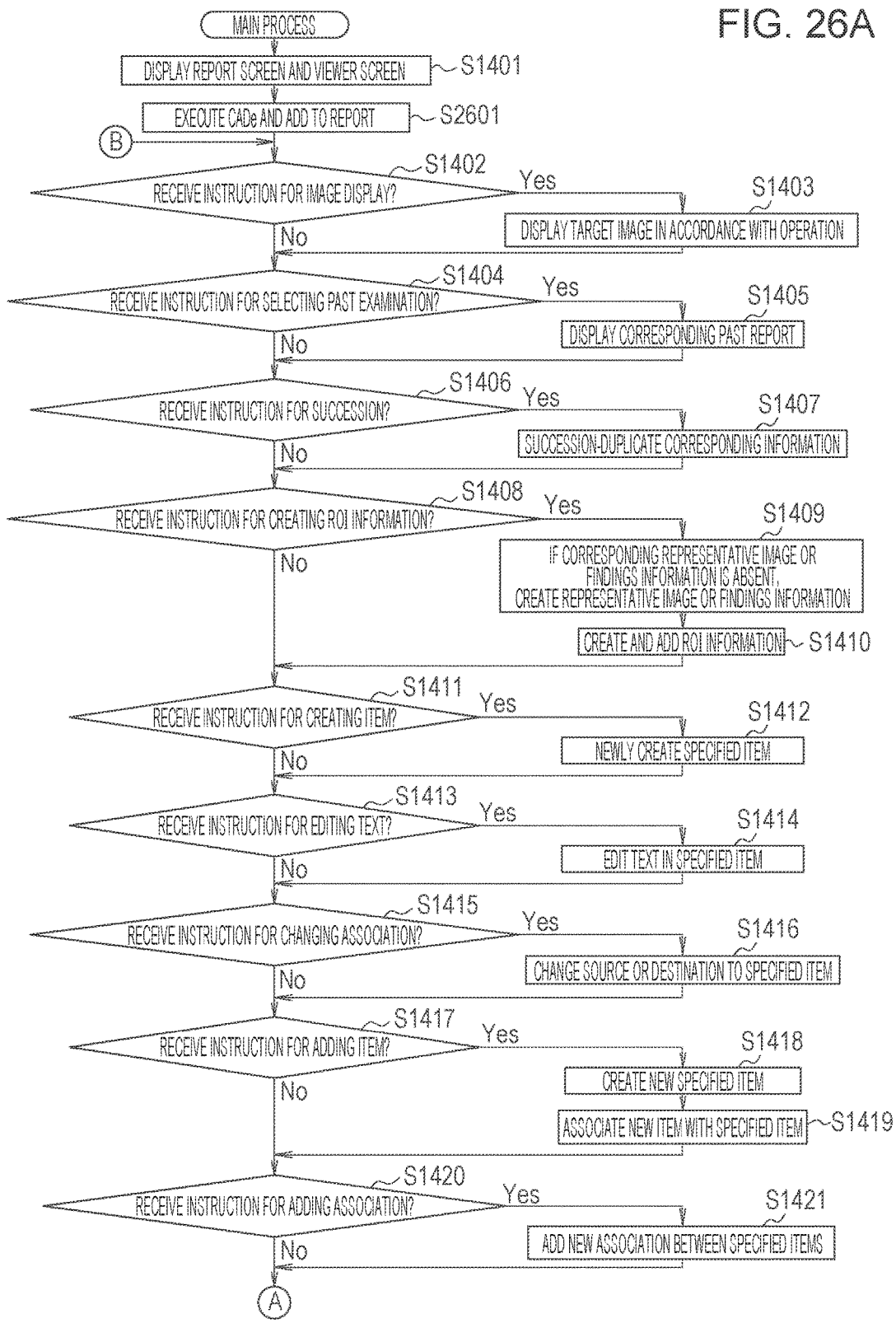
FIGS. 26A and 26B are a flowchart illustrating a main process according to a second embodiment.
Figure 26B:
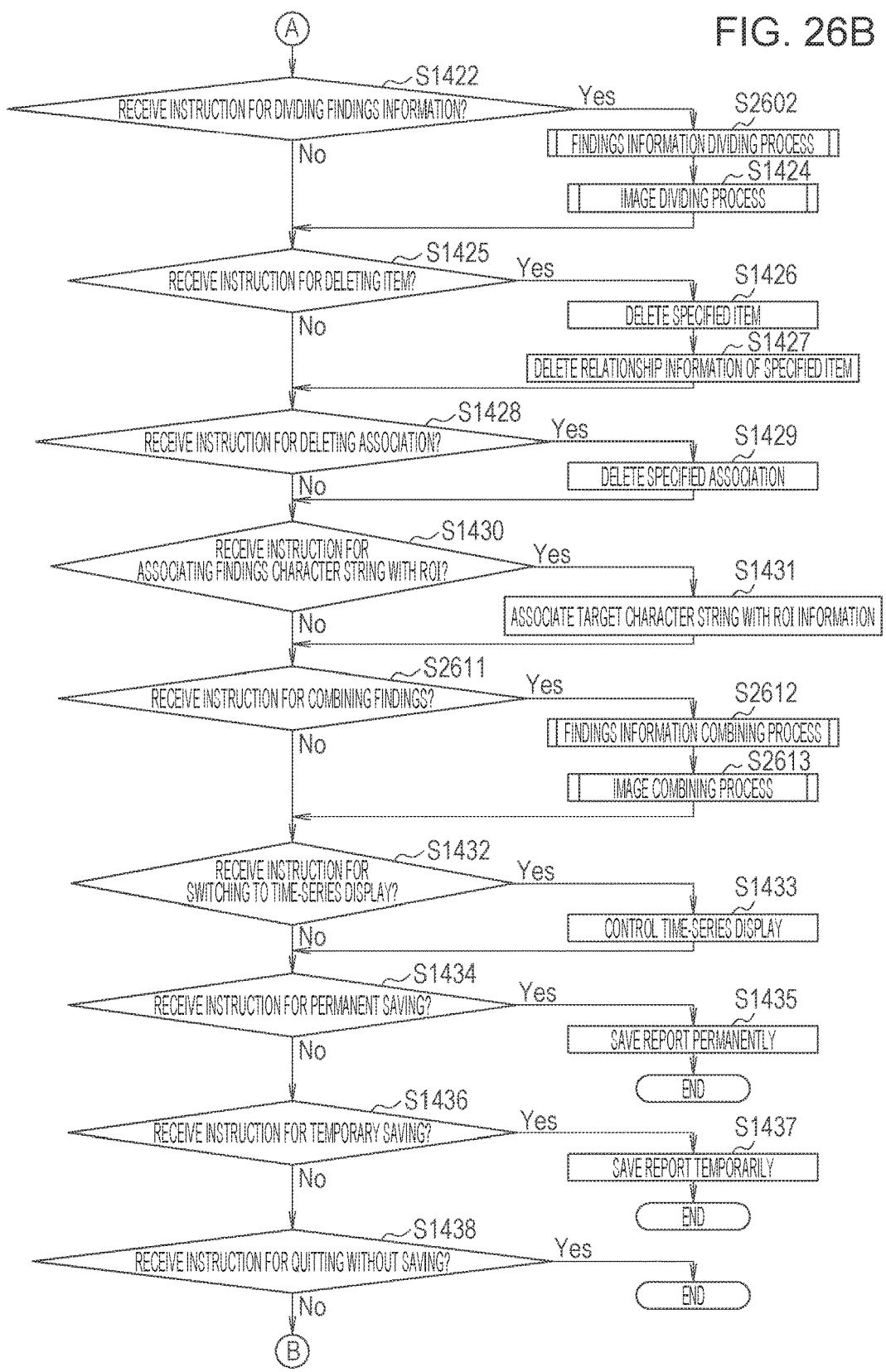

FIGS. 26A and 26B are a flowchart illustrating a main process performed by the terminal apparatus 100 according to the second embodiment. In FIGS. 26A and 26B, the same or substantially the same processing with the processing in the main process according to the first embodiment is denoted by the same reference numeral. After step S1401, the CPU 202 causes the process to proceed to S2601. In step S2601, the editing unit 413 executes CADe on an image that is an examination target. Then, the editing unit 413 adds a lesion detection result to radiographic interpretation report information as findings information and then causes the process to proceed to step S1402. Here, the CADe may be any CADe and is not limited to a specific one.

A findings information dividing process (S2602) in the second embodiment is different from the findings information dividing process (S1423) described in the first embodiment. The findings information dividing process (S2602) will be described later with reference to FIG. 29.

If the determination result in step S1430 is NO, or after step S1431, the CPU 202 causes the process to proceed to step S2611. In step S2611, upon receiving an instruction for combining findings information items (YES in step S2611), the receiving unit 412 causes the process to proceed to step S2612. If an instruction for combining findings information items is not received (NO in step S2611), the receiving unit 412 causes the process to proceed to step S1432. In step S2612, the editing unit 413 performs a findings information combining process. Then, in step S2613, the editing unit 413 performs an image combining process. Note that the findings information combining process (S2612) and the image combining process (S2613) will be described later with reference to FIGS. 27 and 26, respectively.

Figure 27:
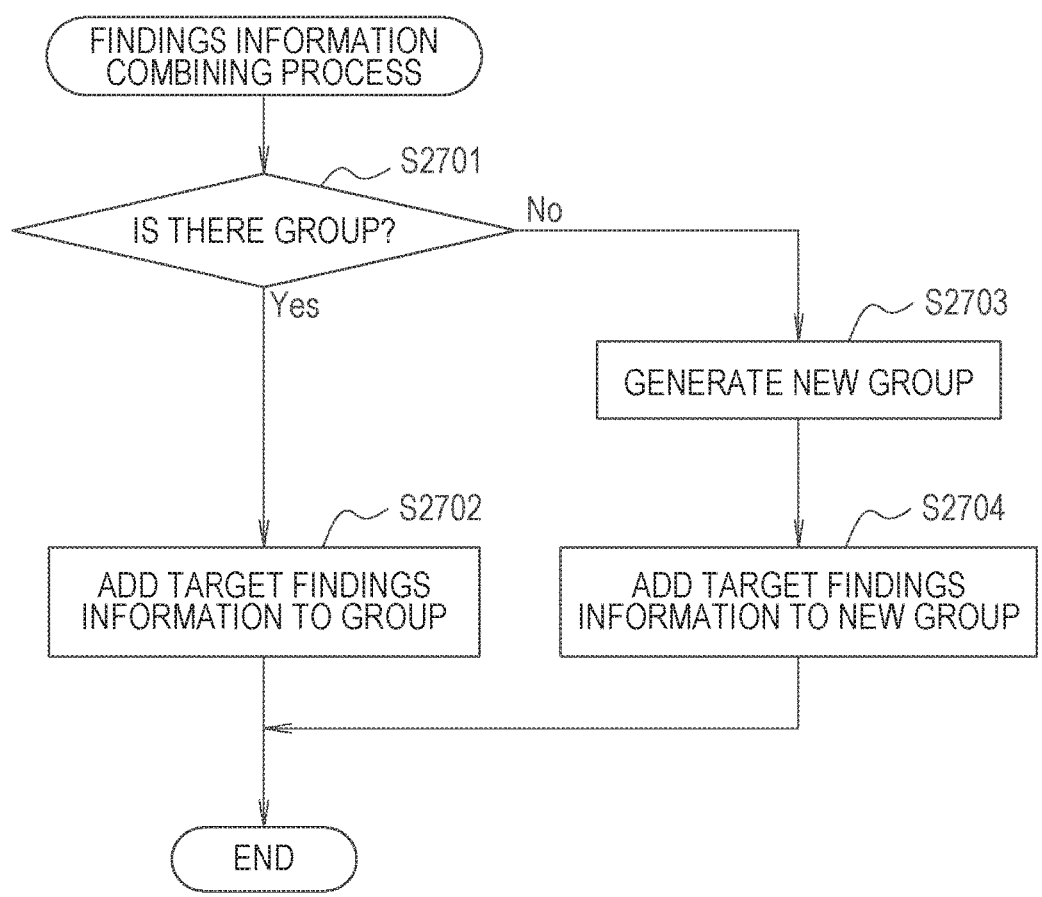
FIG. 27 is a flowchart illustrating a findings information combining process.

FIG. 27 is a flowchart illustrating details of the findings information combining process (S2612) described with reference to FIGS. 26A and 26B. In step S2701, the editing unit 413 determines whether or not there is a group including findings information specified as a combination target. If there is such a group (YES in step S2701), the editing unit 413 causes the process to proceed to step S2702. If there is no such a group (NO in step S2701), the editing unit 413 causes the process to proceed to step S2703. In step S2702, the editing unit 413 adds the findings information that is a combination target to the existing group. Then, the findings information combining process ends.

On the other hand, in step S2703, the editing unit 413 generates a new group of findings information. Then, in step S2704, the editing unit 413 adds the findings information specified as the combination target to the new group generated in step S2703. Then, the findings information combining process ends. Note that if there are a plurality of groups in step S2701, the editing unit 413 combines the groups into one group. In this case, as another example, the editing unit 413 may combine the plurality of groups in a hierarchical manner. In addition, in this case, the editing unit 413 may select one of the two methods above in accordance with a user operation.

Figure 28:
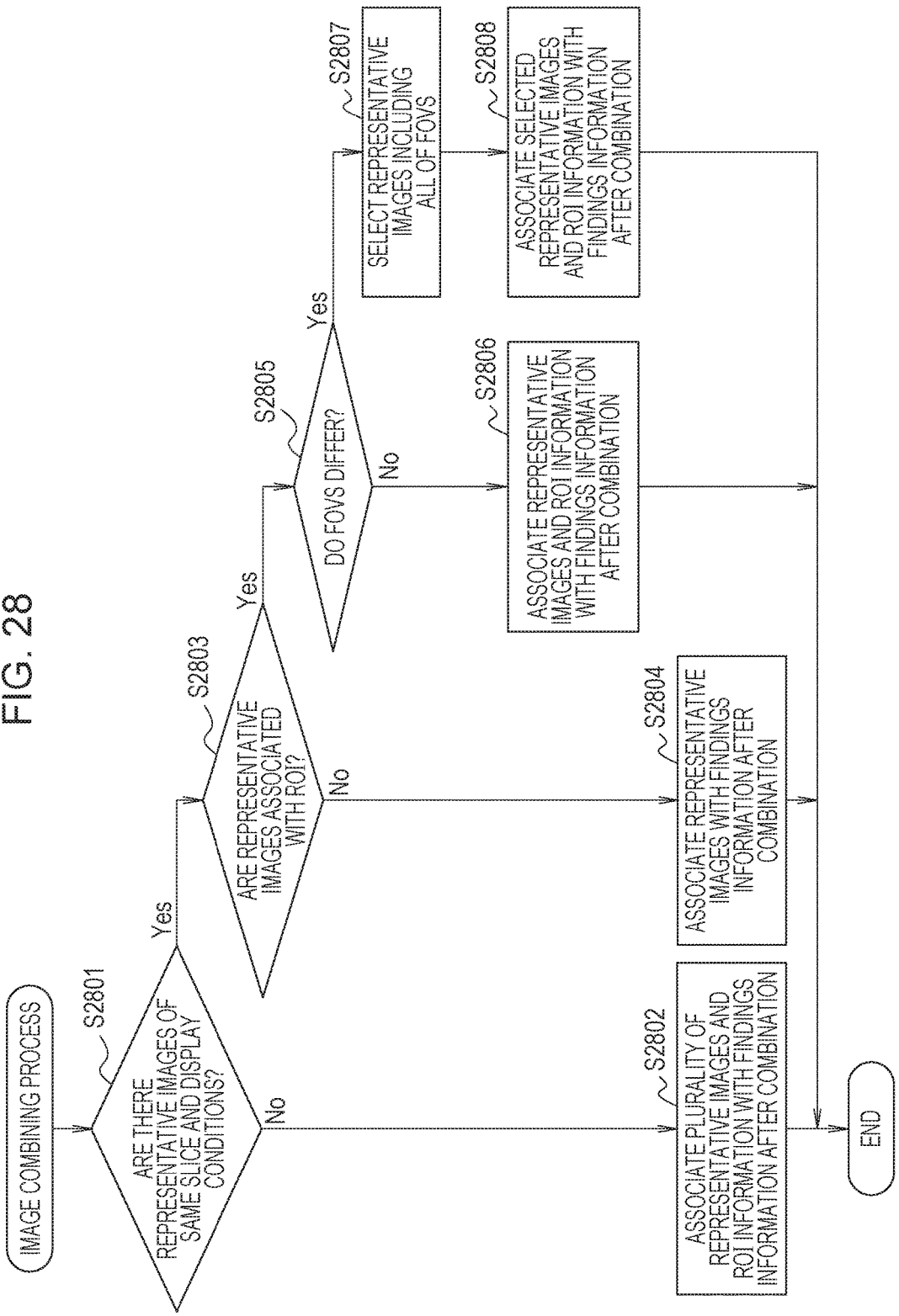
FIG. 28 is a flowchart illustrating an image combining process.

FIG. 28 is a flowchart illustrating details of the image combining process (S2613) described with reference to FIGS. 26A and 26B. In step S2801, the editing unit 413 determines whether or not there are representative images of the same slice image corresponding to the same display conditions among representative images associated with findings information items that are combination targets. If there are representative images of the same slice image corresponding to the same display conditions (YES in step S2801), the editing unit 413 causes the process to proceed to step S2803. If there are no representative images of the same slice image corresponding to the same display conditions (NO in step S2801), the editing unit 413 causes the process to proceed to step S2802.

In step S2802, as described above with reference to FIG. 23, the editing unit 413 associates representative images and ROI information associated with the findings information items that are combination targets with findings information after combination. That is, the editing unit 413 changes association between the representative images, the findings information, and the ROI information. Then, the image combining process ends. Note that the display conditions include the window level and window width at the time of image display.

In step S2803, the editing unit 413 determines whether or not the representative images of the same slice image corresponding to the same display conditions, the representative images having been determined in step S2801, are associated with ROI information. If ROI information is associated (YES in step S2803), the editing unit 413 causes the process to proceed to step S2805. If ROI information is not associated. (NO in step S2803), the editing unit 413 causes the process to proceed to step S2804. In step S2804, the editing unit 413 associates the representative images of the same slice image corresponding to the same display conditions with findings information after combination. Then, the image combining process ends.

In step S2805, the editing unit 413 determines whether or not FOVs differ between the representative images of the same slice image corresponding to the same display conditions. If FOVs differ (YES in step S2805), the editing unit 413 causes the process to proceed to step S2807. If FOVs are the same (NO in step S2805), the editing unit 413 causes the process to proceed to step S2806. In step S2806, the editing unit 413 associates the representative images of the same slice image corresponding to the same display conditions and the ROI information associated with each of the findings information items that are combination targets with findings information after combination. Then, the image combining process ends.

In step S2807, the editing unit 413 selects representative images including all of the FOVs. Then, in step S2808, the editing unit 413 associates the representative images selected in step S2807 and the ROI information associated with each of the findings information items that are combination targets with findings information after combination. Then, the image combining process ends.

Note that there may be a plurality of sets of the representative images of the same slice image corresponding to the same display conditions associated with findings information items that are combination targets. In this case, the editing unit 413 performs processing in step S2803 through step S2808 on each of the sets.

FIG. 29 is a flowchart illustrating details of the findings information dividing process (S2602) described with reference to FIGS. 26A and 26B in step S2901, the editing unit 413 determines whether or not findings information specified as a divide target is findings information included in a group (e.g., findings information detected through CADe). If findings information is not included in a group (NO in step S2901), the editing unit 413 causes the process to proceed to step S1501. Note that the processing in step S1501 through step S1511 is the same or substantially the same as the processing in the findings information dividing process in the first embodiment described with reference to FIG. 15.

If findings information is included in a group (YES in step S2901), the editing unit 413 causes the process to proceed to step S2902. In step S2902, the editing unit 413 determines whether or not there are a plurality of findings information items that are divide targets. If there are a plurality of findings information items (YES in step S2902), the editing unit 413 causes the process to proceed to step S2904. If there are not a plurality of findings information items (NO in step S2902), the editing unit 413 causes the process to proceed to step S2903.

In step S2903, the editing unit 413 divides the group of findings information items to extract the findings information that is the divide target. Specifically, the editing unit 413 deletes the UID of the findings information that is the divide target from the group of findings information items. Then, the editing unit 413 causes the process to proceed to step S1507. In step S2904, the editing unit 413 creates a new group and records the UID of the findings information items specified as divide targets in the new group of findings information items and then causes the process to proceed to step S1507. Note that the other configuration and processing of the medical information display system according to the second embodiment are the same or substantially the same as the configuration and processing of the medical information display system according to the first embodiment.

By using the CADe detection results in the above manner, the terminal apparatus 100 according to the second embodiment does not need to associate a ROI and findings, thereby reducing a load for association. In addition, not only if findings information is divided, but also if findings information items are combined, in response, the terminal apparatus 100 can automatically update association between a representative image and findings information and can automatically update a display status of the association therebetween. In the above manner, even if the group of lesions has been changed, the terminal apparatus 100 can manage medical information such that changes in lesions can be followed over time.

Although embodiments have been described above in detail, the present invention is not limited to such specific embodiments and may be modified or changed in various manners without departing from the scope of the spirit of the present invention described in the Claims.

Other Embodiments

Although the exemplary embodiments have been described above, the present invention can be implemented in an embodiment as a system, an apparatus, a method, a program, a recording medium (storage medium), or the like. Specifically, the present invention is applicable to a system including a plurality of apparatuses (e.g., a host computer, an interface device, an imaging device, and a web application) or an apparatus including a single device.

Embodiments of the present invention can also be realized by a computer of a system or apparatus that reads and executes computer executable instructions (e.g., one or more programs) recorded on a storage medium (which may also be referred to more fully as a 'non-transitory computer-readable storage medium') to perform the functions of one or more of the above-described embodiments and/or that includes one or more circuits (e.g., application specific integrated circuit (ASIC)) for performing the functions of one or more of the above-described embodiments, and by a method performed by the computer of the system or apparatus by, for example, reading out and executing the computer executable instructions from the storage medium to perform the functions of one or more of the above-described embodiments and/or controlling the one or more circuits to perform the functions of one or more of the above-described embodiments. The computer may comprise one or more processors (e.g., central processing unit (CPU), micro processing unit (MPU)) and may include a network of separate computers or separate processors to read and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application. No. 2016-080607 filed Apr. 13, 2016, which is hereby incorporated by reference herein in its entirety.

What is claimed is:

1. An information processing system comprising:
a memory storing instructions; and
one or more processors, that upon execution of the instructions, configure the one or more processors to operate as:
a receiving unit configured to receive a divide instruction for dividing a first medical text corresponding to a first display image representing a target region into a second medical text and a third medical text, wherein the first medical text and the first display image are displayed in association with each other on a display unit; and
a display processing unit configured to, in case where the divide instruction has been received, display the second medical text and the third medical text that are different from the first medical text and to display a second display image in association with the second medical text and a third display image in association with the third medical text on the display unit.

2. The information processing system according to claim 1, wherein the display processing unit depicts the first display image on the basis of a captured image corresponding to the first medical text and the target region in the first display image associated with the first medical text.

3. The information processing system according to claim 1, wherein the display processing unit depicts the first display image on the basis of a captured image corresponding to the first medical text and the target region in the first display image associated with the first medical text.

4. The information processing system according to claim 2, wherein, in a case where the divide instruction has been received, the display processing unit depicts the second display image on the basis of the captured image and the target region corresponding to the second medical text, and the third display image on the basis of the capture image and the target region corresponding to the third medical text.

5. The information processing system according to claim 1, wherein, in a case where the divide instruction has been received, the display processing unit updates the first display image on the basis of the second medical text and the third medical text.

6. The information processing system according to claim 1, wherein the display processing unit displays, as the first display image, an image in which a region image representing the target region in the first display image is superimposed on a captured image.

7. The information processing system according to claim 1, wherein, in a case where the divide instruction has been received, the display processing unit displays, as the second display image and the third display image, an image in which a region image representing the target region corresponding to the second medical text and the third medical text is superimposed on a captured image.

8. The information processing system according to claim 1, wherein, in a case where the divide instruction has been received, the display processing unit deletes, from the first display image, a region image representing the target region corresponding to the second medical text and the third medical text, the region image being displayed by being superimposed on a captured image.

9. The information processing system according to claim 8, wherein the region image is a display frame defining the target region.

10. The information processing system according to claim 8, wherein the region image is an image indicating identification information of the target region.

11. The information processing system according to claim 1, wherein, if a plurality of target regions represented by a plurality of first display images are associated with the first medical text, the display processing unit displays the first medical text and each of the plurality of first display images in association with each other.

12. The information processing system according to claim 11, wherein, in a case where the divide instruction has been received, the display processing unit deletes association between the first medical text and at least one of first display images representing a corresponding target region corresponding to the second medical text and the third medical text.

13. The information processing system according to claim 1, further comprising:
a storage unit configured to store a captured image, the first medical text, and the target region corresponding to the first medical text in association with one another,
wherein the display processing unit displays the first display image and the first medical text in association with each other by referring to information in the storage unit.

14. The information processing system according to claim 13, wherein
the storage unit stores, in a case where the divide instruction has been received, the second medical text and the third medical text and the target region corresponding to the second medical text and the third medical text in association with the captured image.

15. The information processing system according to claim 1,
wherein, if a plurality of medical text items and a plurality of display images are displayed in association with each other on the display unit, the receiving unit receives an instruction for combining the plurality of medical text items, and
wherein the display processing unit displays the combined medical text items as new medical text and displays a display image representing a target region corresponding to the combined medical text items in association with the combined medical text items.

16. The information processing system according to claim 1, wherein the medical text is findings information.

17. An information processing system comprising:
a memory storing instructions; and
one or more processors, that upon execution of the instructions, configure the one or more processors to operate as:
a receiving unit configured to receive a divide instruction for dividing a first medical text corresponding to a first display image representing a target region into a second medical text and a third medical text, wherein the first medical text and the first display image are displayed in association with each other on a display unit; and
a display processing unit configured to, in case where the divide instruction has been received, display the second medical text and the third medical text that are different on the display unit,
wherein, if a plurality of target regions represented by a plurality of first display images are associated with the first medical text, the display processing unit displays the first medical text and each of the plurality of first display images in association with each other, wherein, in a case where the divide instruction has been received, the display processing unit displays at least one of the plurality of first display images in association with the second medical text and a second display images in association with the third medical text on the display unit.

18. An information processing method performed by an information processing system, comprising:
receiving a divide instruction for dividing a first medical text corresponding to a first display image representing a target region into a second medical text and a third medical text, wherein the first medical text and the first display image are displayed in association with each other on a display; and
upon receiving the divide instruction, displaying the second medical text and the third medical text that are different from the first medical text on the display and to displaying a second display in association with the second medical text and a third image in association with the third medical text on the display.

19. A non-transitory computer readable storage medium that stores instructions that, when executed by one or more processors, causes a computer to perform a method, the method comprising:
receiving a divide instruction for dividing a first medical text corresponding to a first display image representing a target region into a second medical text and a third medical text, wherein the first medical text and the first display image are displayed in association with each other on a display; and
upon receiving the divide instruction, displaying the second medical text and the third medical text that are different from the first medical text on the display and to displaying a second display in association with the second medical text and a third image in association with the third medical text on the display.

* * * * *